United States Patent
Hedrich et al.

(10) Patent No.: US 9,375,505 B2
(45) Date of Patent: *Jun. 28, 2016

(54) HEMOSTATIC SPONGE

(71) Applicants: Baxter International Inc., Deerfield, IL (US); Baxter Healthcare S.A., Glattpark (Opfikon) (CH)

(72) Inventors: Hans Christian Hedrich, Vienna (AT); Joris Hoefinghoff, Vienna (AT)

(73) Assignees: Baxter International Inc., Deerfield, IL (US); Baxter Healthcare, S.A., Glattpark (Opfikon) (CH)

( * ) Notice: Subject to any disclaimer, the term of this patent is extended or adjusted under 35 U.S.C. 154(b) by 85 days.

This patent is subject to a terminal disclaimer.

(21) Appl. No.: 14/184,543

(22) Filed: Feb. 19, 2014

(65) Prior Publication Data
US 2014/0308325 A1     Oct. 16, 2014

Related U.S. Application Data

(63) Continuation of application No. 13/082,114, filed on Apr. 7, 2011, now Pat. No. 8,703,170.

(60) Provisional application No. 61/321,661, filed on Apr. 7, 2010, provisional application No. 61/424,031, filed on Dec. 16, 2010.

(51) Int. Cl.
| | |
|---|---|
| *A61F 13/36* | (2006.01) |
| *A61L 15/26* | (2006.01) |
| *A61L 24/00* | (2006.01) |
| *A61L 15/32* | (2006.01) |
| *A61L 15/42* | (2006.01) |

(52) U.S. Cl.
CPC ............ *A61L 15/26* (2013.01); *A61L 15/325* (2013.01); *A61L 15/425* (2013.01); *A61L 24/0036* (2013.01); *A61L 24/0094* (2013.01); *A61L 2400/04* (2013.01)

(58) Field of Classification Search
CPC ................. A61L 24/0036; A61L 2400/04
See application file for complete search history.

(56) References Cited

U.S. PATENT DOCUMENTS

| 2,507,244 A | 5/1950 | Correll |
| 2,558,395 A | 6/1951 | Studer |

(Continued)

FOREIGN PATENT DOCUMENTS

| CN | 1270240 A | 10/2000 |
| EP | 0132983 A | 2/1985 |

(Continued)

OTHER PUBLICATIONS

Ansell et al., "Gelfoam and Autologous Clot Embolization: Effect on Coagulation", *Invest. Radiol.* (1978) 13:115-120.

(Continued)

*Primary Examiner* — Susan Su
(74) *Attorney, Agent, or Firm* — Kilpatrick Townsend & Stockton LLP

(57) ABSTRACT

The present invention provides a hemostatic porous composite sponge comprising
i) a matrix of a biomaterial and
ii) one hydrophilic polymeric component comprising reactive groups
wherein i) and ii) are associated with each other so that the reactivity of the polymeric component is retained, wherein associated means that
said polymeric component is coated onto a surface of said matrix of a biomaterial, or
said matrix is impregnated with said polymeric material, or both.

27 Claims, 9 Drawing Sheets

(56) References Cited

U.S. PATENT DOCUMENTS

| | | |
|---|---|---|
| 3,089,815 A | 5/1963 | Kupelwieser et al. |
| 4,006,220 A | 2/1977 | Gottlieb |
| 4,013,078 A | 3/1977 | Field |
| 4,124,705 A | 11/1978 | Rothman et al. |
| 4,164,559 A | 8/1979 | Miyata et al. |
| 4,179,400 A | 12/1979 | Tsao et al. |
| 4,265,233 A | 5/1981 | Sugitachi et al. |
| 4,291,013 A | 9/1981 | Wahlig et al. |
| 4,292,972 A | 10/1981 | Pawelchak et al. |
| 4,298,598 A | 11/1981 | Schwarz et al. |
| 4,300,494 A | 11/1981 | Graiff et al. |
| 4,347,234 A | 8/1982 | Wahlig et al. |
| 4,362,567 A | 12/1982 | Schwarz et al. |
| 4,377,572 A | 3/1983 | Schwarz et al. |
| 4,424,208 A | 1/1984 | Wallace et al. |
| 4,453,939 A | 6/1984 | Zimmerman et al. |
| 4,482,386 A | 11/1984 | Wittwer et al. |
| 4,515,637 A | 5/1985 | Cioca |
| 4,536,387 A | 8/1985 | Sakamoto et al. |
| 4,540,410 A | 9/1985 | Wood et al. |
| 4,543,332 A | 9/1985 | Jao et al. |
| 4,554,156 A | 11/1985 | Fischer et al. |
| 4,600,574 A | 7/1986 | Lindner et al. |
| 4,640,834 A | 2/1987 | Eibl et al. |
| 4,655,211 A | 4/1987 | Sakamoto et al. |
| 4,746,514 A | 5/1988 | Warne |
| 4,749,689 A | 6/1988 | Miyata et al. |
| 4,803,075 A | 2/1989 | Wallace et al. |
| 4,818,517 A | 4/1989 | Kwee et al. |
| 4,832,686 A | 5/1989 | Anderson |
| 4,837,285 A | 6/1989 | Berg et al. |
| 4,885,161 A | 12/1989 | Cornell |
| 4,891,359 A | 1/1990 | Saferstein et al. |
| 4,925,677 A | 5/1990 | Feijen |
| 4,946,870 A | 8/1990 | Partain, III. et al. |
| 5,007,916 A | 4/1991 | Linsky et al. |
| 5,017,229 A | 5/1991 | Burns et al. |
| 5,023,082 A | 6/1991 | Friedman et al. |
| 5,041,292 A | 8/1991 | Feijen |
| 5,061,274 A | 10/1991 | Kensey |
| 5,061,492 A | 10/1991 | Okada et al. |
| 5,080,893 A | 1/1992 | Goldberg et al. |
| 5,108,421 A | 4/1992 | Fowler |
| 5,126,141 A | 6/1992 | Henry |
| 5,129,882 A | 7/1992 | Weldon et al. |
| 5,134,229 A | 7/1992 | Saferstein et al. |
| 5,135,751 A | 8/1992 | Henry et al. |
| 5,135,755 A | 8/1992 | Czech et al. |
| 5,140,016 A | 8/1992 | Goldberg et al. |
| 5,149,540 A | 9/1992 | Kunihiro |
| 5,162,430 A | 11/1992 | Rhee et al. |
| 5,165,938 A | 11/1992 | Knighton |
| 5,178,883 A | 1/1993 | Knighton |
| 5,192,300 A | 3/1993 | Fowler |
| 5,196,185 A | 3/1993 | Silver et al. |
| 5,204,382 A | 4/1993 | Wallace et al. |
| 5,209,776 A | 5/1993 | Bass et al. |
| 5,219,328 A | 6/1993 | Morse et al. |
| 5,275,616 A | 1/1994 | Fowler |
| 5,292,362 A | 3/1994 | Bass et al. |
| 5,300,494 A | 4/1994 | Brode, II et al. |
| 5,304,377 A | 4/1994 | Yamada et al. |
| 5,306,501 A | 4/1994 | Viegas et al. |
| 5,324,775 A | 6/1994 | Rhee et al. |
| 5,328,955 A | 7/1994 | Rhee et al. |
| 5,330,446 A | 7/1994 | Weldon et al. |
| 5,350,573 A | 9/1994 | Goldberg et al. |
| 5,352,715 A | 10/1994 | Wallace et al. |
| 5,356,614 A | 10/1994 | Sharma |
| 5,384,333 A | 1/1995 | Davis et al. |
| 5,385,606 A | 1/1995 | Kowanko |
| 5,399,361 A | 3/1995 | Song et al. |
| 5,418,222 A | 5/1995 | Song et al. |
| 5,428,022 A | 6/1995 | Palefsky et al. |
| 5,428,024 A | 6/1995 | Chu et al. |
| 5,437,672 A | 8/1995 | Allyne |
| 5,447,966 A | 9/1995 | Hermes et al. |
| 5,478,352 A | 12/1995 | Fowler |
| 5,507,744 A | 4/1996 | Tay et al. |
| 5,510,418 A | 4/1996 | Rhee et al. |
| 5,512,301 A | 4/1996 | Song et al. |
| 5,514,379 A | 5/1996 | Weissleder et al. |
| 5,516,532 A | 5/1996 | Atala et al. |
| 5,520,925 A | 5/1996 | Maser |
| 5,531,759 A | 7/1996 | Kensey et al. |
| 5,540,715 A | 7/1996 | Katsaros et al. |
| 5,580,923 A | 12/1996 | Yeung et al. |
| 5,595,735 A | 1/1997 | Saferstein et al. |
| 5,614,587 A | 3/1997 | Rhee et al. |
| 5,618,551 A | 4/1997 | Tardy et al. |
| 5,648,506 A | 7/1997 | Desai et al. |
| 5,658,592 A | 8/1997 | Tanihara et al. |
| 5,667,839 A | 9/1997 | Berg |
| 5,672,336 A | 9/1997 | Sharma |
| 5,674,275 A | 10/1997 | Tang et al. |
| 5,690,675 A | 11/1997 | Sawyer et al. |
| 5,698,213 A | 12/1997 | Jamiolkowski et al. |
| 5,714,370 A | 2/1998 | Eibl et al. |
| 5,752,974 A | 5/1998 | Rhee et al. |
| 5,770,229 A | 6/1998 | Tanihara et al. |
| 5,853,749 A | 12/1998 | Hobbs |
| 5,856,356 A | 1/1999 | Tsouderos et al. |
| 5,861,043 A | 1/1999 | Carn |
| 5,863,984 A | 1/1999 | Doillon et al. |
| 5,874,500 A | 2/1999 | Rhee et al. |
| 5,902,832 A | 5/1999 | Van Bladel et al. |
| 5,908,054 A | 6/1999 | Safabash et al. |
| 5,931,165 A | 8/1999 | Reich et al. |
| 5,959,735 A | 9/1999 | Maris et al. |
| 5,997,895 A | 12/1999 | Narotam et al. |
| 6,063,061 A | 5/2000 | Wallace et al. |
| 6,066,325 A | 5/2000 | Wallace et al. |
| 6,110,484 A | 8/2000 | Sierra |
| 6,129,761 A | 10/2000 | Hubbell |
| 6,132,759 A | 10/2000 | Schacht et al. |
| 6,166,130 A | 12/2000 | Rhee et al. |
| 6,179,872 B1 | 1/2001 | Bell et al. |
| 6,277,394 B1 | 8/2001 | Sierra |
| 6,287,341 B1 | 9/2001 | Lee et al. |
| 6,312,474 B1 | 11/2001 | Francis et al. |
| 6,312,725 B1 | 11/2001 | Wallace et al. |
| 6,328,229 B1 | 12/2001 | Duronio et al. |
| 6,338,810 B1 | 1/2002 | Carpena et al. |
| 6,458,386 B1 | 10/2002 | Schacht et al. |
| 6,458,889 B1 | 10/2002 | Trollsas |
| 6,495,127 B1 | 12/2002 | Wallace et al. |
| 6,624,245 B2 | 9/2003 | Wallace et al. |
| 6,649,162 B1 | 11/2003 | Biering et al. |
| 6,706,690 B2 | 3/2004 | Reich et al. |
| 6,730,299 B1 * | 5/2004 | Tayot .............. A61L 15/32 424/124 |
| 6,831,058 B1 | 12/2004 | Ikada et al. |
| 7,320,962 B2 | 1/2008 | Reich et al. |
| 7,435,425 B2 | 10/2008 | Qian et al. |
| 7,547,446 B2 | 6/2009 | Qian et al. |
| 7,871,637 B2 | 1/2011 | Qian et al. |
| 8,303,981 B2 | 11/2012 | Wallace et al. |
| 8,357,378 B2 | 1/2013 | Wallace et al. |
| 2002/0081732 A1 * | 6/2002 | Bowlin .............. A61F 2/08 435/446 |
| 2002/0165337 A1 | 11/2002 | Wallace et al. |
| 2002/0193448 A1 | 12/2002 | Wallace et al. |
| 2003/0064109 A1 | 4/2003 | Qian et al. |
| 2004/0147465 A1 | 7/2004 | Jiang et al. |
| 2005/0277577 A1 | 12/2005 | Hunter et al. |
| 2005/0281883 A1 | 12/2005 | Daniloff et al. |
| 2006/0147492 A1 | 7/2006 | Hunter et al. |
| 2006/0167561 A1 | 7/2006 | Odar et al. |
| 2006/0258560 A1 | 11/2006 | Yang et al. |
| 2008/0085316 A1 | 4/2008 | Qian et al. |
| 2008/0091277 A1 | 4/2008 | Deusch et al. |
| 2008/0132468 A1 | 6/2008 | Cullen |
| 2008/0187591 A1 | 8/2008 | Rhee et al. |
| 2008/0241072 A1 | 10/2008 | Barry et al. |

(56) References Cited

U.S. PATENT DOCUMENTS

| | | | |
|---|---|---|---|
| 2008/0286376 | A1 | 11/2008 | Qian et al. |
| 2009/0142396 | A1 | 6/2009 | Odar et al. |
| 2010/0028309 | A1 | 2/2010 | Odar et al. |
| 2010/0292717 | A1 | 11/2010 | Petter-Puchner et al. |
| 2010/0297235 | A1 | 11/2010 | Hnojewyj |
| 2010/0318048 | A1 | 12/2010 | Hoefinghoff et al. |
| 2011/0021964 | A1* | 1/2011 | Larsen ............. A61L 26/0066 602/47 |
| 2011/0104280 | A1 | 5/2011 | Hnojewyj |
| 2011/0202026 | A1 | 8/2011 | Hedrich et al. |
| 2011/0251574 | A1 | 10/2011 | Hedrich et al. |
| 2012/0101519 | A1 | 4/2012 | Hill et al. |
| 2012/0207813 | A1 | 8/2012 | Rhee et al. |

FOREIGN PATENT DOCUMENTS

| | | |
|---|---|---|
| EP | 0282316 A2 | 9/1988 |
| EP | 0376931 | 7/1990 |
| EP | 0132983 B2 | 12/1991 |
| EP | 0493387 | 7/1992 |
| EP | 0891193 | 1/1999 |
| EP | 0612252 B1 | 5/1999 |
| EP | 1084720 A1 | 3/2001 |
| EP | 1283063 A2 | 2/2003 |
| EP | 1484070 A1 | 12/2004 |
| EP | 1414370 B1 | 4/2007 |
| JP | 51-125156 | 11/1976 |
| JP | 59-113889 | 6/1984 |
| JP | 05308969 | 11/1993 |
| JP | 6-254148 | 9/1994 |
| JP | 08-024325 | 1/1996 |
| JP | 9-504719 | 5/1997 |
| JP | 07090241 A | 4/2007 |
| KR | 10-1991-0007847 B1 | 10/1991 |
| WO | 86/00912 | 2/1986 |
| WO | 90/13320 A1 | 11/1990 |
| WO | 92/21354 | 12/1992 |
| WO | 92/22252 | 12/1992 |
| WO | 94/27630 A1 | 12/1994 |
| WO | 95/12371 | 5/1995 |
| WO | 96/04025 | 2/1996 |
| WO | 96/06883 | 3/1996 |
| WO | 96/10374 | 4/1996 |
| WO | 96/10428 | 4/1996 |
| WO | 96/14368 | 5/1996 |
| WO | 96/39159 | 12/1996 |
| WO | 97/22371 | 6/1997 |
| WO | 97/37694 A1 | 10/1997 |
| WO | 98/08550 A1 | 3/1998 |
| WO | 99/13902 A1 | 3/1999 |
| WO | 02/22059 A1 | 3/2002 |
| WO | 02/22184 A2 | 3/2002 |
| WO | 02/070594 A2 | 9/2002 |
| WO | 02/072128 A1 | 9/2002 |
| WO | 03/007845 A1 | 1/2003 |
| WO | 03/103734 | 12/2003 |
| WO | 2004/028404 A2 | 4/2004 |
| WO | 2004/108179 A1 | 12/2004 |
| WO | 2006/031358 A | 3/2006 |
| WO | 2006/118460 A1 | 11/2006 |
| WO | 2007/001926 A2 | 1/2007 |
| WO | 2007/137839 A2 | 12/2007 |
| WO | 2007/137839 A3 | 12/2007 |
| WO | 2008/016983 A2 | 2/2008 |

OTHER PUBLICATIONS

Barrow, D.L., et al.; "The Use of Greater Omentum Vascularized Free Flaps for Neurosurgical Disorders Requiring Reconstruction"; J. Neurosurg.; vol. 60; pp. 305-311 (Feb. 1984).

Barton et al., "Fibrin Glue as a Biologic Vascular Patch—A Comparative Study" (abstract posted at http://www.ncbi.nlm.nih.gov/ on Jan. 3, 2001 from) *J. Surg. Res.* (1986) 40(5): 510-513.

Baxter product brochure for TissuFleece E, TissuCone E and TissuFoil E (2003).

Baxter Product Catalogue; Collagen; 4 pages (2006).

Baxter, "GentaFleece Collagen Fleece—Version 5 : Collagen Sponge with antibiotic protection for surgical use," Retrieved from http://www.advancingbiosurgery.com/en_EU/downloads/ifu_gentafleece.pdf, Mar. 2002, 2 pages. English portion second column of first page.

Boyers et al., "Reduction of Postoperative Pelvic Adhesions in the Rabbit with Gore-Tex Surguical Membrane" *Fert. Ster.* (1988) 49(6):1066-1070.

Bruck, S. D., Ed., "Controlled Drug Delivery", Crc Press, Boca Raton, FL (1983) A title page and table of contents.

Cantor et al., "Gelfoam and Thrombin in Gastrointestinal Bleeding: An Experimental Study." *Journal of Laboratory and Clinical Medicine* vol. 35, No. 6 (1950): pp. 890-893.

Cantor et al., "Gelfoam and Thrombin in Treatment of Massive Gastroduodenal Hemmorhage: A Preliminary Report" *Am J. Surg.* (1950) pp. 883-887.

Cantor et al., "Gelfoam and Thrombin in Treatment of Massive Upper Gastroduodenal Hemorrhage", *Am. J. Surg.* (1951) pp. 230-235.

Chaplin, J.M., et al.; "Use of an Acellular Dermal Allograft for Dural Replacement: An Experimental Study"; Neurosurgery: vol. 45:2; pp. 320-327 (Aug. 1999).

Chuang, et al., "Sheath Needle for Liver Biopsy in High Risk Patients", *Radiology* (1988) 166:261-262.

Cheung, David T., et al., "Mechanism of crosslinking of proteins by glutaraldehyde IV: In Vitro and In Vivo stability of a crosslinked collagen matrix", Connective Tissue Research, 1990;25(1), pp. 27-34.

Christensen, et al., "Qualitative Description of the Wurster-Based Fluid-Bed Coating Process." Drug Development and Industrial Pharmacy, vol. 23, No. 5, pp. 451-463, 1997.

Collins et al., "Enemata of Gelfoam-Milk Suspension Combined with Thrombin Solution to Control Massive Hemorrhage Following Anorectal Surgery", *Am. J. Proctol.* (1951) 2:60-63.

Collins, Ronald et al., "Use of Collagen Film as a Dural Substitute: Preliminary Animal Studies", *Journal of Biomedical Materials Research* vol. 25, 267-276 (1991).

Edgerton et al., "Vascular Hamartomas and Hemangiomos: Classification and Treatment" *Southern Med. J.* (1982) 75(12):1541-1547.

EPC Examination Report dated Oct. 2, 2013 for European Patent Application #11712579.9 (Publication No. EP 2555804 (A1) published Feb. 13, 2013).

Filippi, R., et al.; "Bovine Pericardium for Duraplasty: Clinical Results in 32 Patients"; Neurosurg. Rev.; vol. 20; pp. 103-107 (2001).

First Examination Report for New Zealand Patent #602630 filed Sep. 25, 2012 mailed May 30, 2013.

Gibble, et al., "Fibrin glue: the perfect operative sealant?" Reviews, Transfusion, 1990, pp. 741-747, vol. 30 No. 8.

Guoping, Chen et al. "Scaffold Design for Tissue Engineering," Macromol. Biosci., pp. 67-77, 2002.

Heller et al., " Release of Norethindrone from Poly(Ortho Esters)" *Polymer Engineering Sci.* (1981) 21:727-731.

Hieb, Lee D. et al., "Spontaneous Postoperative Cerebrospinal Fluid Leaks Following Application of Anti-Adhesion Barrier Gel", SPINE vol. 26, No. 7, pp. 748-751, 2001.

Hood et al., "Efficacy of Topical Hemostat Floseal Matrix in Vascular Surgery," 24th World Congress of the International Society for Cardiovascular Surgery (Sep. 12-16, 1999), 2 pages total.

Hotz et al., "Collagen and Fibrin as Biologic Binders from Granular Hydroxyapatite" (abstract posted at http://www.ncbi.nlm.nih.gov/ on Jan. 3, 2001 from) *Dtsh. Z. Mund. Kiefer Geichtshir.* (1989) 13(4):296-300.

International Search Report of PCT/EP2011/055418 mailed on May 31, 2011, 3 pages.

Jeong et al., "Biodegradable Block Copolymers as Injectible Drig-Delivery Systems" *Nature* (1997) 388:860-862.

Jonas, Richard A., et al., "A new sealant for knitted Dacron prostheses: Minimally cross-linked gelatin", J. Vasc. Surg., Mar. 1988;7(3), pp. 414-419.

Kim, Kee D., et al., "Reduction in Leg Pain and Lower-Extremity Weakness with Oxiplex/SP Gel for 1 Year after Laminactomy, Laminotomy, and Disectomy", Neurosurg Focus 17 (1): Clinical Pearl 1, Jul. 2004, pp. 1-6.

(56) References Cited

OTHER PUBLICATIONS

Kline, D.G.; "Dural Replacement with Resorbable Collagen"; Arch Surg; vol. 91; pp. 924-929 (Dec. 1965).
Knopp, U., "A new collagen foil versus a cadaveric dura graft for dural defects—a comparative animal experimental study", EANS—12th European Congress of Neurosurgery, Lisbon, Sep. 7-12, 2003, 663-666.
Kofidis, T., et al., "Clinically established Hemostatis Scaffold (Tissue Fleece) as Biomatrix in Tissue- and organ-engineering research", Tissue Eng vol. 9, No. 3, 2003, S.517-523; ISSN: 1076-3279.
Krill et al., "Topical Thrombin and Powdered Gelfoam: An Efficiaent Hemostatic Treatment for Surgery", J. Tenn. Dent. Assoc. (1986) 66(2):26-27.
Kuhn, J. et al., "Bilateral Subdural Haemotomata and Lumbar Pseudomeningocele Due to a Chronic Leakage of Liquor Cerebrospinalis after a Lumbar Disectomy with the Application of ADCON-L Gel", J. Neural Neurosurg. Psychiarty 2005; 76: 1031-1033.
Langer et al., "Chemical and Physical Structure of Polymerns as Carriers for Controlled Release of Bioactive Agents: A Review" Rev. Marco Chem. Phys. (1983) C23(1):61-126.
Laquerriere, A., et al.; "Experimental Evaluation of Bilayered Human Collagen as a Dural Substitute"; J. Neurosurg; vol. 78; pp. 487-491 (Mar. 1993).
Larson, Paul O., "Topical Hemostatic Agents for Dermatologic Surgery", J. Dermatol. Surg. Oncol., Jun. 1988;14(6), pp. 623-632.
Le, Anh X. et al., "Unrecognized Durotomy After Lumbar Discectomy: A Report of Four Cases Associated with the Use of ADCON-L", SPINE vol. 26, No. 1, pp. 115-118, 2001.
Lee, J.F., et al.; "Experimental Evaluation of Silicone-Coated Dacron and Collagen Fabric-Film Laminate as Dural Substitutes"; J. Neurosurg.; vol. 27; pp. 558-564 (Apr. 1967).
Leong et al., "Polyanhydrides for Controlled Release of Bioactive Agents" Biomaterials (1986) 7:364-371.
Leong et al., "Polymeric Controlled Drug Delivery" Adv. Drug Delivery Rev. (1987)1:199-233.
Maok, "Hemostatic Agents" (1991) Today's O.R. Nurse, pp. 6-10.
Masar et al., "Synthesis of Polyurethanes and Investigation of their Hydrolytic Stability" J. Polymer. Sci., Polymer Symposium (1979) 66:259-268.
Matsumoto, K., et al.; "A Gelatin Coated Collagen-Polyglycolic Acid Composite Membrane as a Dural Substitute"; ASAIO Journal; pp. 641-645 (2001).
Maurer, P.K., et al.; "Vicryl (Polyglactin 910) Mesh as a Dural Substitute"; J Neurosurg; vol. 63; pp. 448-452 (Sep. 1985).
McClure et al., "Massive Gastroduodenal Hemorrhage: Treatment with Powdered Gelfoam and Buffered Thrombin Solution" Surg. (1952) 32:630-637.
McPherson, J. M. et al., "An examination of the biologic response to injectable, glutaraldehyde cross-linked collagen implants", J. Biomed. Mater. Res., Jan. 1986;20(1), pp. 93-107.
McPherson, J. M., et al., "The preparation and physiochemical characterization of an injectable form of reconstituted, glutaraldehyde cross-linked, bovine corium collagen", J. Biomed. Mater. Res., Jan. 1986;20(1), pp. 79-92.
McPherson, John M., et al., "The Effects of Heparin on the Physiochemical Properties of Reconstituted Collagen", Coll. Relat. Res., Jan. 1988;8(1), pp. 65-82.
Meddings, N., et al.; "Collagen Vicryl—A New Dural Prosthesis"; Acta Neurochir; vol. 117; pp. 53-58 (1992).
Mello, L.R., et al., "Duraplasty with Biosynthetic Cellulose: An Experimental Study"; J Neurosurg; vol. 86; pp. 143-150 (Jan. 1997).
Narotam, P.K., et al.; "A Clinicopathological Study of Collagen Sponge as a Dural Graft in Neurosurgery"; J Neurosurg; vol. 82; pp. 406-412 (Mar. 1995).
Narotam, P.K., et al., "Experimental Evaluation of Collagen Sponge as a Dural Graft"; British Journal of Neurosurgery; vol. 7; pp. 635-641 (1993).

Nimni, M. E., et al., "Chemically modified collagen: A natural biomaterial for tissue replacement", J. Biomed. Mater. Res., Jun. 1987;21(6), pp. 741-71.
Nimni, Marcel E., "The cross-linking and structure modification of the collagen matrix in the design of cardiovascular prosthesis", J. of Cardiac Surgery, Dec. 1988;3(4), pp. 523-33.
Notification of Transmittal of the International Preliminary Report on Patentability for PCT/EP201/055418 dated Jul. 27, 2012.
O'Neill, P., et al.; "Use ofPorcine Dermis as Dural Substitute in 72 Patients"; J. Neurosurg.; vol. 61;pp. 351-354 (Aug. 1984).
Palm, S.J., et al.; "Dural Closure with Nonpenetrating Clips Prevents Meningoneural Adhesions: An Experimental Study in Dogs"; Neurosurgery; vol. 45:4; pp. 875-882 (Oct. 1999).
Parizek, J., et al.; "Detailed Evaluation of 2959 Allogeneic and Xenogeneic Dense Connective Tissue Grafts (Fascia Lata, Pericardium, and Dura Mater) Used in the Course of 20 Years for Duraplasty in Neurosurgery"; Acta Neurochir; vol. 139; pp. 827-838 (1997).
Park, Y-K., at al.; "Prevention of Arachnoiditis and Postoperative Tethering of the Spinal Cord with Gore-Tex Surgical Membrane: An Experimental Study with Rats"; Neurosurgery; vol. 42 :4; pp. 813-824 (Apr. 1998).
PCT International Preliminary Report on Patentability and Written Opinion mailed Feb. 17, 2009, International Application No. PCT/US2007/074984, 8 pages.
Pietrucha, K.; "New Collagen Implant as Dural Substitute"; Biomatarials; vol. 12; pp. 320-323 (Apr. 1991).
Pitt et al., "Controlled Release of Bioactive Materials", R. Baker, Ed., Academic Press, New York, 1980.
Porchet, Francois, "Inhibition of Epidural Fibrosis with ADCON-L: Effect on Clinical Outcome One Year Following Re-operation for Recurrent Lumbar Radiculopathy", 1998, pp. 1-10.
Raul, J.S., et al.; "Utilisation du Polyester Urethane (NEURO-PATCH®) Comme Substitut Dural"; Neurochirugie; vol. 49:2-3; pp. 83-89 (2003), English abstract only on p. 83.
Reddy, M., et al.; "A Clinical Study of a Fibrinogen-Based Collagen Fleece for Dural Repair in Neurosurgery"; Acta Neurochir; vol. 144; pp. 265-269 (2002).
Riley et al., "Percutaneous Liver Biopsy with Plugging of Needle Track: A Safe Method for Use in Patients with Impaired Coagulation" Lancet (Aug. 25, 1984) pp. 436.
Rosenblatt, Joel, et al., "Effect of electrostatic forces on the dynamic rheological properties of injectable collagen biomaterials", Biomaterials, 1992;13(12), pp. 878-86.
Rosenblatt, Joel, et al., "Injectable collagen as a pH-sensitive hydrogel", Biomaterials, Oct. 1994;15(12), pp. 985-995.
Ross, Jeffrey S. et al., "Association Between Peridural Scar and Recurrent Radicular PAIN After Lumbar Discectomy: Magnetic Resonance Evaluation", Neurosurgery, pp. 855-863, 1996.
Rossler, B., et al., "Collagen microparticles: preparation and properties", J. Microencapsulation, Jan.-Feb. 1995;12(1), pp. 49-57.
San-Galli, F., et al.; "Experimental Evaluation of a Collagen-Coated Vicryl Mesh as a Dural Substitute"; Neurosurgery: vol. 30:3; pp. 396-401 (1992).
Shaffrey, C.I., et al.; "Neurosurgical Applications of Fibrin Glue: Augmentation ofDural Closure in 134 Patients"; Neurosurgery; vol. 26:2; pp. 207-210 (1990).
Sidman et al., "Biodegradable, Implantable Sustained Release Systems Based on Glutamic Acid Copolymers" J. Membrane Science (1979) 7:227-291.
Smith, KA, et al.; "Delayed Postoperative Tethering of the Cervical Spinal Corei"; J Neurosurg; vol. 81; pp. 196-201 (Aug. 1994).
Springorum, H.W.; "Die Verwendung von Kollagenfolien zur Uberbruckung von Defekten des Gleitgewebes bei Achillotenotomien and Achillessehnenrupturen"; Akt. Traumatal.; vol. 15; pp. 120-121 (1985), English abstract only on p. 120.
Stricker, A., et al.; "Die Verwendung von TissuFoil Membran bei der Sinusbodenaugmentation"; Ellipse; vol. 17:1; pp. 1-5 (2001), English abstract only on p. 1.
Sugitachi et al., "A Newly Devised Chemo-embolic Agent, G.T. XIII-ADM." (English abstract posted at http://www.ncbi.nlm.nih.gov/ on Jan. 3, 2001 from) Gan. To. Kagaku Ryoho. (1985) 12(10) 1942-1943.

(56) References Cited

OTHER PUBLICATIONS

Sugitachi et al., "Locoregional Therapy in Patients with Maignant Pleural Effusion—Two Different Kinds of BAC Therapy" (English abstract posted at http://www.ncbi.nlm.nih.gov/ on Jan. 3, 2001 from) *Gan. To. Kagaku Ryoho.* (1992) 19(10):1640-1643.

Sugitachi et al., "Preoperative Transcatheter Arterial Chemoembolization for Locally Advanced Breast Cancer: Application for New Thrombotic Materials" *Japan J. Surg.* (1983) 13(5):456-458.

Taguchi, et al., "Encapsulation of chondrocytes in injectable alkali-treated collagen gels prepared using poly(ethylene glycol)-based 4-armed star polymer", *Biomaterials,* vol. 26, 2005, pp. 1247-1252.

TissuFleece E, Version 5, Package Leaflet, Baxter International Inc., 2003, 8 pages, English portion of instructions for use.

Tobin et al., "Plugged Liver Biopsy in Patients with Impaired Coagulation" *Digestive Diseases and Science* (1989) 34(1):13-15.

Tucker et al., "Absorbable Gelatin (Gelfoam) Sponge" Charles T. Thomas, Publisher, Springfiled, Illinois, 3-125. 1965.

Vander Salm et al., "Reduction of Sternal Infection by Application of Topical Vancomycin" *J. Thorac. Surg.* (1989) 98:618-622.

Vinas, F.E., et al.; "Evaluation of Expanded Polytetrafluoroethylene (ePTFE) versus Polydioxanone (PDS) for the Repair ofDura Mater Defects"; Neurological Research; vol. 21; pp. 262-268 (Apr. 1999).

Wallace, Donald G., et al., "Injectable cross-linked collagen with improved flow properties", J. of Biomedical Materials Research, Aug. 1989;23(8), pp. 931-945.

Wallace, Donald, "The relative contribution of electrostatic interactions to stabilization of collagen fibrils", Biopolymers, May-Jun. 1990; 29(6-7), pp. 1015-1026.

Wang, X., et al., "A Comparison of Chitosan and Collagen Sponges as Hemostatic Dressings", *Journal of Bioactive and Compatible Polymers* vol. 21 (2006): pp. 39-54.

Warren, W.L., et al.; Dural Repair Using Acellular Human Dermis: Experience with 200 Cases: Technique Assessment; Neurosurgery; vol. 46:6; pp. 1391-1396 (Jun. 2000).

Wonganan, et al., "PEGylated Adenoviruses: From Mice to Monkeys", *Viruses,* vol. 2, 2010, pp. 468-502.

Written Opinion of the International Searching Authority for PCT/EP2011/055418 dated May 31, 2011.

Yuki et al., "Effects of Endoscopic Variceal Sclerotherapy using GT XIII on Blood Coagulation Tests and the Renal Kallikrein-kinin System" (English abstract posted at http://www.ncbi.nlm.nih.gov/ on Jan. 3, 2001 from) *Gastroentral. Japan* (1990) 25(5):561-567.

Ziegelaar, B.W. et al., "The characterisation of human respiratory epithelial cells cultured on reabsorbable scaffolds: first steps towards a tissue engineered tracheal replacement", Biomaterials 23 (2002), 1425-1438; ISSN 0142-9612.

Ziegelaar, B.W.; "Tissue Engineering of a Tracheal Equivalent", Doctoral Thesis at Ludwig Maximilians University, Munich, Germany; 25 pages (2004).

Zins et al., "US-Guided Percutaneous Liver Biopsy with Plugging of the Needle Track: A Prospective Study in 72 High-Risk Patients" *Radiology* (1992) 184(3):841-843.

\* cited by examiner

HEMOSTATIC SPONGE

CROSS REFERENCE TO RELATED APPLICATION

This application is a continuation of U.S. patent application Ser. No. 13/082,114 filed on Apr. 7, 2011, which is a nonprovisional of, and claims the benefit of U.S. Provisional Application No. 61/321,661, filed Apr. 7, 2010, and U.S. Provisional Application No. 61/424,031, filed Dec. 16, 2010, entitled "HEMOSTATIC SPONGE," the entire disclosures of which are incorporated herein by reference for all purposes.

FIELD OF THE INVENTION

The present invention relates to the field of hemostatic sponges, a method of producing said sponges and their various uses.

BACKGROUND OF THE INVENTION

Biological glues based on coagulation factors of human or animal origin have long been known. A method for producing tissue adhesives based on fibrinogen and factor XIII has been described in U.S. Pat. Nos. 4,362,567, 4,298,598 and 4,377,572. The tissue adhesives are usually applied together with a separate component containing thrombin, which is enzymatically acting on fibrinogen to form fibrin, and on factor XIII to form the active factor XIIIa, which cross-links the fibrin to obtain a stable fibrin clot.

Collagen pads have been used for many years to improve wound healing or to stop bleeding. Their mechanism of action in hemostasis is based on platelets aggregation and activation, the formation of thrombin on the surface of activated platelets and the formation of a hemostatic fibrin clot by the catalytic action of thrombin on fibrinogen. To improve the hemostatic action of collagen pads or sheets it has been suggested to include factors of hemostasis within such pads.

In U.S. Pat. No. 4,600,574 a tissue adhesive based on collagen combined with fibrinogen and factor XIII is described. This material is provided in the lyophilized form, ready for use. The fibrinogen and factor XIII are combined with the collagen by impregnating the collagenous flat material with a solution comprising fibrinogen and factor XIII, and lyophilizing said material.

WO 97/37694 discloses a hemostatic sponge based on collagen and an activator or proactivator of blood coagulation homogeneously distributed therein. This sponge is provided in a dry form, which could be air-dried or lyophilized. However, it still contains a water content of at least 2%.

U.S. Pat. No. 5,614,587 discusses bioadhesive compositions comprising cross-linked collagen using a multifunctionally activated synthetic hydrophilic polymer, as well as methods of using such compositions to effect adhesion between a first surface and a second surface, wherein at least one of the first and second surfaces can be a native tissue surface.

WO2004028404 describes a tissue sealant composed of a synthetic collagen or gelatin and a electrophilic cross-linking agent which are provided in a dry state. Upon wetting of this composition at an appropriate pH a reaction between the 2 components takes place and a gel with sealing properties is formed. Such a sealant works in essential analogously to other known two component sealants (composed of a reagent with multiple electrophilic- and a reagent with multiple nucleophilic groups) which are known in the state of the art or which are available on the market, e.g. Coseal™. In a special embodiment of the invention the two components of the sealant (the electrophilic cross-linker and the synthetic collagen/gelatin) are coated onto a biomaterial.

Collagen-containing compositions which have been mechanically disrupted to alter their physical properties are described in U.S. Pat. No. 5,428,024, U.S. Pat. No. 5,352,715, and U.S. Pat. No. 5,204,382. These patents generally relate to fibrillar and insoluble collagens. An injectable collagen composition is described in U.S. Pat. No. 4,803,075. An injectable bone/cartilage composition is described in U.S. Pat. No. 5,516,532. A collagen-based delivery matrix comprising dry particles in the size range from 5 µm to 850 µm which may be suspended in water and which has a particular surface charge density is described in WO 96/39159. A collagen preparation having a particle size from 1 µm to 50 µm useful as an aerosol spray to form a wound dressing is described in U.S. Pat. No. 5,196,185. Other patents describing collagen compositions include U.S. Pat. No. 5,672,336 and U.S. Pat. No. 5,356,614.

SUMMARY OF THE INVENTION

The subject of the invention is a hemostatic porous composite sponge comprising
i) a matrix of a biomaterial and
ii) one hydrophilic polymeric component comprising reactive groups
wherein i) and ii) are associated with each other so that the reactivity of the polymeric component is retained, wherein associated means that
said polymeric component is coated onto a surface of said matrix of a biomaterial, or
said matrix is impregnated with said polymeric material, or both.

It has been found that previous pads of fibrous biomaterials, in particular collagen pads, for wound healing failed to induce hemostasis at conditions with impaired hemostasis (e.g. after heparinization). The sponge according to the present invention improves hemostasis. Furthermore, the sponge according to the present invention shows a strong adherence to the tissue when applied to a wound. The sponge of the present invention further shows improved swelling behavior, i.e. low swelling, after application to a wound.

A further aspect relates to a method of treating an injury comprising administering a hemostatic porous composite sponge to the site of injury.

Also provided is a kit for preparing a wound coverage, comprising a sponge as herein disclosed and a buffer solution. This kit and its components are in particular for the manufacture of a medical sponge for the treatment of an injury.

In one aspect, embodiments of the present invention encompass a hemostatic porous composite sponge. Exemplary sponges may include a matrix of a biomaterial and one hydrophilic polymeric component having reactive groups. The biomaterial and polymeric component can be associated with each other so that the reactivity of the polymeric component is retained. The biomaterial and polymeric component can be associated so that the polymeric component is coated onto a surface of said matrix of a biomaterial, or so that the matrix is impregnated with the polymeric material, or both. The biomaterial can include collagen, gelatin, fibrin, a polysaccharide, e.g. chitosan, a synthetic biodegradable biomaterial, e.g. polylactic acid or polyglycolic acid, and derivatives thereof. The hydrophilic polymer can be a polyalkylene oxide polymer, esp. preferred a PEG comprising polymer. e.g. a multi-electrophilic polyalkylene oxide polymer, e.g. a multi-electrophilic PEG, such as pentaerythritolpoly(ethyleneglycol)ether tetrasuccinimidyl glutarate. In some cases, the biomaterial can be collagen and the polymeric component can be pentaerythritolpoly(ethyleneglycol)ether tetrasuccinimidyl glutarate. The polymeric form can be coated onto the collagen. In some cases, the biomaterial is collagen and the polymeric component is pentaerythritolpoly(ethyleneglycol) ether tetrasuccinimidyl glutarate, and the polymeric form is impregnated into the collagen.

In another aspect, embodiments of the present invention encompass the use of a sponge as described herein for the treatment of an injury such as a wound, a hemorrhage, damaged tissue and/or bleeding tissue. Embodiments also encompass methods of treating an injury such as a wound, a hemorrhage, damaged tissue and/or bleeding tissue. Exemplary methods of treating an injury may include administering a hemostatic sponge as described herein to the site of injury. In some instances, the sponge is applied to the injury together with a buffer solution, e.g. a bicarbonate solution, e.g. on a gauze.

In a further aspect, embodiments of the present invention include kits. For example, a kit may include one or more sponges as described herein, and a buffer solution, e.g. an alkaline buffer solution, such as a bicarbonate, together with instructions for its use.

In still another aspect, embodiments of the present invention encompass methods of manufacturing a hemostatic sponge. Exemplary methods may include, for example, providing a sponge having a matrix of a biomaterial in dried form, providing at least one reactive polymeric material in the form of dry powder, contacting the sponge or biomaterial and the polymeric material so that the polymeric material is present on at least one surface of the sponge, and fixing the polymeric material on the sponge. In some cases, the process of fixing can be achieved by melting at temperatures between 30° C. to 80° C., preferably between 60° C. to 65° C., for a time period sufficient for fixing, preferably between 1 minute to 10 minutes, especially about 4 minutes. In yet another aspect, embodiments of the present invention encompass methods for manufacturing a hemostatic sponge which may include providing a sponge having a matrix of a biomaterial in dried form, providing a reactive polymeric material in the form of a solution, contacting the sponge or biomaterial and the polymeric material so that the sponge or biomaterial is impregnated with the polymeric material, and drying the impregnated biomaterial. Exemplary embodiments further encompass sponges obtainable by the manufacturing methods described herein.

In another aspect, embodiments of the present invention encompass a hemostatic composite having a haemostatic material and a hydrophilic polymeric crosslinker with reactive groups. The composite can have pores which allow external fluids, especially human blood, to access into the composite. In some hemostatic composite embodiments, the haemostatic material is a non-woven or woven fabric of a haemostatic fiber or a porous haemostatic sponge. In some cases, the haemostatic material is a collagen sponge, a fabric of oxidized cellulose, a fibrin sponge, or a gelatin sponge. Embodiments of the present invention further encompass hemostatic composites where the hydrophilic polymeric crosslinker with reactive groups is a polyethylene glycol (PEG), preferably a PEG comprising two or more reactive from succinimidylesters (—CON(COCH$_2$)$_2$), aldehydes (—CHO) and isocyanates (—N═C═O), especially preferred succinimidylesters.

All patent filings, scientific journals, books, treatises, and other publications and materials discussed in this application are hereby incorporated by reference for all purposes. While the exemplary embodiments have been described in some detail, by way of example and for clarity of understanding, those of skill in the art will recognize that a variety of modification, adaptations, and changes may be employed. Therefore, the scope of the present invention is limited solely by the claims.

Those skilled in the art will readily understand that all preferred embodiments disclosed in the following are examples of specific embodiments, but are not necessarily limiting the general inventive concept. Furthermore, all special embodiments can be read on all inventive aspects and embodiments in any combination, if not mutually exclusive. All equivalents or obvious alterations or modifications as recognized by those skilled in the art are included by the present invention.

DETAILED DESCRIPTION OF THE INVENTION

The object of the invention is a hemostatic porous composite sponge comprising a hemostatic porous composite sponge comprising
i) a matrix of a biomaterial and
ii) one hydrophilic polymeric component comprising reactive groups
wherein i) and ii) are associated with each other so that the reactivity of the polymeric component is retained, wherein associated means that
    said polymeric component is coated onto a surface of said matrix of a biomaterial, e.g. as a continuous or discontinuous layer on at least one surface of said sponge, or
    said matrix is impregnated with said polymeric material or both.

The term impregnated as meant herein includes the term absorption of polymeric material in a matrix of a biomaterial.

The terms sponge, pad and fleece are used interchangeably in the description of the present invention.

Preferably the biomaterial is collagen, a protein, a biopolymer, or a polysaccharide. Especially preferred is a biomaterial selected from the group consisting of collagen, gelatin (especially cross-linked gelatin), fibrin, a polysaccharide (especially chitosan, oxidized cellulose, aldehyde activated dextrans, starch based polyaldehydes (obtainable by periodate oxidation)), a synthetic biodegradable biomaterial (especially polylactic acid or polyglycolic acid, and derivatives thereof, more preferred collagen.

According to the present invention a porous composite material comprising a water insoluble matrix of a biomaterial with hemostatic properties and a hydrophilic polymeric cross-linking agent in association therewith is provided.

Upon contact with bleeding tissue, a cross-linking reaction of the hydrophilic polymeric cross-linker with the blood proteins leads to formation of a gel with sealing and hemostatic properties. Cross-linking also occurs to the tissue surface proteins and, depending on the nature of the water insoluble matrix biomaterial, may also occur to the matrix biomaterial. The latter reaction contributes to an improved adhesion of the composite material to the wounded tissue surface. Furthermore, it is important for the hemostatic efficacy of the composite according to the present invention that the matrix of the biomaterial has soaking capabilities, i.e. is able to soak/absorb liquids such as blood, serum, plasma.

Such soaking capabilities are especially dependent on the hydrophilic nature of the polymer the matrix is made of, and a three-dimensional structure of open interconnected pores, or of a three-dimensional meshwork of hydrophilic fibers. The pore size and the elasticity of the matrix are also important for the soaking capacity. Elasticity means that the matrix can be compressed in aqueous solution and returns to its initial volume after the force causing compression is relieved.

The sponge is a porous network of a biomaterial able to absorb body fluids when applied to the site of an injury. This allows the blood of a wound (including all the blood components, such as blood cells or coagulation proteins) to enter into the sponge. The porous sponge according to the present invention has therefore an inside volume which is accessible for external fluids, such as blood, when applied to a patient. For example, a porous collagen sponge can be made by lyophilization of a collagen gel, suspension or solution by freeze-drying (whereas normal air-drying leads to a collagen film). It follows that in the case of collagen, the resulting porous sponge according to the present invention has typically from 5 to 100 mg collagen/cm$^3$, whereas collagen films have from 650 to 800 mg collagen/cm$^3$. If external fluids, such as blood get in contact with the sponge according to the present invention, the hydrophilic polymeric component comprising reactive groups can react with the blood components and/or with the surface of the matrix of the biomaterial so as to crosslink the components which bind to the (at least two) reactive groups. Furthermore, the sponge is usually flexible and suitable to be applied on diverse tissues and locations with various shapes.

The collagen used for the present invention can be from any collagen material including liquid, pasty, fibrous or powdery materials that can be processed to a porous, especially a porous and fibrous matrix. The preparation of a collagen gel for the production of a sponge is e.g. described in the EP 0891193 (incorporated herein by reference) and may include acidification until gel formation occurs and subsequent pH neutralization. To improve gel forming capabilities or solubility the collagen may be (partially) hydrolyzed or modified, as long as the property to form a stable sponge when dried is not diminished.

The collagen or gelatin of the sponge matrix is preferably of animal origin, preferably bovine or equine. However, also human collagen might be used in case of a hypersensitivity of the patient towards xenogenic proteins. Also synthetic or recombinant collagen may be used. The further components of the sponge are preferably of human origin, which makes the sponge suitable especially for the application to a human.

In a preferred embodiment the porous collagen sponge contains about 5 to about 50, e.g. about 10 to about 30, preferably about 25 mg collagen/cm$^3$ of dry sponge.

The biomaterial may be non-crosslinked or crosslinked, preferably the biomaterial has been crosslinked.

The hydrophilic polymeric component of the sponge according to the present invention is a hydrophilic crosslinker which is able to react with its reactive groups once the sponge is applied to a patient (e.g. to a wound of a patient or another place where the patient is in need of a hemostatic activity). Therefore it is important for the present invention that the reactive groups of the polymeric component are reactive when applied to the patient. It is therefore necessary to manufacture the sponge according to the present invention so that the reactive groups of the polymeric component which should react once they are applied to a wound are retained during the manufacturing process.

This can be done in various ways. For example, usual hydrophilic polymeric components have reactive groups which are susceptible to hydrolysis after contact with water. Accordingly, premature contact with water or aqueous liquids has to be prevented before administration of the sponge to the patient, especially during manufacture. However, processing of the hydrophilic polymeric component during manufacturing may be possible also in an aqueous medium at conditions where the reactions of the reactive groups are inhibited (e.g. at a low pH). If the hydrophilic polymeric components can be melted, the melted hydrophilic polymeric components can be sprayed or printed onto the matrix of the biopolymer. It is also possible to sprinkle a dry form (e.g. a powder) of the hydrophilic polymeric component onto the matrix. If necessary, then an increase of the temperature can be applied to melt the sprinkled hydrophilic polymeric component to the matrix to achieve a permanent coating of the sponge. Alternatively, these hydrophilic polymeric components can be taken up into inert organic solvents (inert vis-à-vis the reactive groups of the hydrophilic polymeric components) and brought onto the matrix of the biomaterial. Examples of such organic solvents are dry ethanol, dry acetone or dry dichloromethane (which are e.g. inert for hydrophilic polymeric components, such as NHS-ester substituted PEGs).

In a preferred embodiment the hydrophilic polymer component is a single hydrophilic polymer component and is a polyalkylene oxide polymer, esp. preferred a PEG comprising polymer, in the following called "the material". The reactive groups of said material are preferably electrophilic groups.

The material may be a multi-electrophilic polyalkylene oxide polymer, e.g. a multi-electrophilic PEG. The material can include two or more electrophilic groups such as —CON(COCH$_2$)$_2$, —CHO, —N=C=O, and/or —N(COCH$_2$)$_2$, e.g. a component as disclosed in the WO2008/016983 (incorporated herein by reference in its entirety) and one of the components of the commercially available ones under the trademark CoSeal®.

Preferred electrophilic groups of the hydrophilic polymeric crosslinker according to the present invention are groups reactive to the amino-, carboxy-, thiol- and hydroxy-groups of proteins, or mixtures thereof.

Preferred amino group-specific reactive groups are NHS-ester groups, imidoester groups, aldehyde-groups, carboxy-groups in the presence of carbodiimdes, isocyanates, or THPP (beta-[Tris(hydroxymethyl)phosphino]propionic acid), especially preferred is Pentaerythritolpoly(ethyleneglycol)ether tetrasuccinimidyl glutarate (=Pentaerythritol tetrakis[1-1'-oxo-5'-succinimidylpentanoate-2-poly-oxoethyleneglycole-jether (=an NHS-PEG with MW 10,000).

Preferred carboxy-group specific reactive groups are amino-groups in the presence of carbodiimides.

Preferred thiol group-specific reactive groups are maleiimides or haloacetyls.

Preferred hydroxy group-specific reactive group is the isocyanate group. The reactive groups on the hydrophilic crosslinker may be identical (homo-functional) or different (hetero-functional). The hydrophilic polymeric component can have two reactive groups (homo-bifunctional or heterobifunctional) or more (homo/hetero-trifunctional or more).

In special embodiments the material is a synthetic polymer, preferably comprising PEG. The polymer can be a derivative of PEG comprising active side groups suitable for crosslinking and adherence to a tissue.

By the reactive groups the hydrophilic polymer has the ability to cross-link blood proteins and also tissue surface proteins. Cross-linking to the biomaterial is also possible.

The multi-electrophilic polyalkylene oxide may include two or more succinimidyl groups. The multi-electrophilic polyalkylene oxide may include two or more maleimidyl groups.

Preferably, the multi-electrophilic polyalkylene oxide is a polyethylene glycol or a derivative thereof.

In a most preferred embodiment the polymeric component is pentaerythritolpoly(ethyleneglycol)ether tetrasuccinimidyl glutarate (=COH102, also pentaerythritol tetrakis[1-1'-oxo-5'-succinimidylpentanoate-2-poly-oxoethyleneglycole] ether).

In one preferred embodiment the sponge of the present invention comprises collagen as the biomaterial and the polymeric component, e.g. COH102, is coated onto the surface of the collagen (=coated form).
Especially preferred the coating is a discontinuous coating, e.g. such as shown in FIG. 6.

In another preferred embodiment the coating is a thin continuous coating, as obtained e.g. by spraying the polymeric component from the melt onto the matrix of biomaterial. Such a coating is comparable to a film-like or glass-like structure, e.g. such as shown in FIG. 7.

In another preferred embodiment the sponge of the present invention comprises collagen as the biomaterial and the polymeric component, e.g. COH102, is impregnated into the collagen (=impregnated form).

The molecular weight of the polymeric component is preferably in a range of 500 to 50000, most preferred about 10000.

The amount of coating of polymeric component on the sponge of said biomaterial is preferably from about 1 mg/cm$^2$ to about 20 mg/cm$^2$, more preferred about 2 mg/cm$^2$ to about 14 mg/cm$^2$ for the coated sponge. The concentration of polymeric component is preferably from about 5 mg/cm$^3$ to about 100 mg/cm$^3$, more preferred from about 100 mg/cm$^3$ to about 70 mg/cm$^3$ for an impregnated sponge.

In another preferred embodiment the sponge of the present invention comprises a combination of impregnated and coated forms. Further, the sponge according to the present invention preserves reactivity of the reactive groups of the hydrophilic polymeric component comprising reactive groups by being dry. e.g. having an overall water content of below 10%, especially below 2%, and especially below 1% in case the polymeric component has hydrolysable reactive groups, e.g. NHS-PEG. Higher water contents (e.g. higher than 10%) would also result in a functional sponge but storage stability would be worsened. Accordingly, water contents of below 2% (w/w) are preferred; below 1% is even more preferred; below 0.5% is specifically preferred.

In another preferred embodiment a further layer of a further biomaterial is present. The further layer can be from the same biomaterial as the matrix or it can be a different biomaterial, e.g. matrix of biomaterial is collagen and the further layer is oxidized cellulose. All combinations of biomaterials as mentioned above may be included.

The sponge as a whole can be biodegradable, being suitable for biological decomposition in vivo, or bioresorbable, i.e. able to be resorbed in vivo, e.g. via degradation by proteases which are present in vivo and groups which are hydrolyseable in vivo. Full resorption means that no significant extracellular fragments remain. A biodegradable material differs from a non-biodegradable material in that a biodegradable material can be biologically decomposed into units which may either be removed from the biological system and/or chemically incorporated into the biological system. In a preferred embodiment the particular material, the matrix material or sponge as a whole can be degraded by a subject, in particular a human subject, in less than 6 month, less than 3 month, less than 1 month, less than 2 weeks.

The sponge may further comprise an activator or proactivator of blood coagulation, including fibrinogen, thrombin or a thrombin precursor, as e.g. disclosed in U.S. Pat. No. 5,714,370 (incorporated herein by reference). Thrombin or the precursor of thrombin is understood as a protein that has thrombin activity and that induces thrombin activity when it is contacted with blood or after application to the patient, respectively. Its activity is expressed as thrombin activity (NIH-Unit) or thrombin equivalent activity developing the corresponding NIH-Unit. The activity in the sponge can be 100-10.000, preferably 500-5.000. In the following thrombin activity is understood to comprise both, the activity of thrombin or any equivalent activity. A protein with thrombin activity might be selected from the group consisting of alpha-thrombin, meizothrombin, a thrombin derivative or a recombinant thrombin. A suitable precursor is possibly selected from the group consisting of: prothrombin, factor Xa optionally together with phospholipids, factor IXa, activated prothrombin complex, FETBA, any activator or a proactivator of the intrinsic or extrinsic coagulation, or mixtures thereof.

The hemostatic sponge according to the invention might be used together with further physiologic substances. For example, the sponge preferably further comprises pharmacologically active substances, among them antifibrinolytics, such as a plasminogenactivator-inhibitor or a plasmin inhibitor or an inactivator of fibrinolytics. A preferred antifibrinolytic is selected from the group consisting of aprotinin or an aprotinin derivative, alpha2-macroglobulin, an inhibitor or inactivator of protein C or activated protein C, a substrate mimic binding to plasmin that acts competitively with natural substrates, and an antibody inhibiting fibrinolytic activity.

As a further pharmacologically active substance an antibiotic, such as an antibacterial or antimycotic might be used together with the sponge according to the invention, preferably as a component homogeneously distributed in the sponge. Further bioactive substances such as growth factors and/or pain killers may be also present in the inventive sponge. Such a sponge might be useful in e.g. wound healing.

Further combinations are preferred with specific enzymes or enzyme inhibitors, which may regulate, i.e. accelerate or inhibit, the resorption of the sponge. Among those are collagenase, its enhancers or inhibitors. Also, a suitable preservative may be used together with the sponge or may be contained in the sponge.

Although a preferred embodiment relates to the use of the hemostatic sponge which contains the activator or proactivator of blood coagulation as the only active component, further substances that influence the velocity of blood coagulation, hemostasis and quality of the sealing, such as tensile strength, inner (adhesive) strength and durability might be comprised.

Procoagulants that enhance or improve the intrinsic or extrinsic coagulation, such as factors or cofactors of blood coagulation, factor XIII, tissue factor, prothrombin complex, activated prothrombin complex, or parts of the complexes, a prothrombinase complex, phospholipids and calcium ions, protamin, might be used. In case of a surgical procedure where a precise sealing is needed, it might be preferable to prolong the working period after the hemostatic sponge is applied to the patient and before clotting is affected. The prolongation of the clotting reaction will be ensured, if the sponge according to the invention further comprises inhibitors of blood coagulation in appropriate amounts. Inhibitors, such as antithrombin III optionally together with heparin, or any other serine protease inhibitor, are preferred.

It is also preferred to have such additives, in particular the thrombin or a precursor of thrombin evenly distributed in the material in order to prevent local instability or hypercoagulability of the material. Even with a certain water content the thrombin activity is surprisingly stable, probably because of the intimate contact of thrombin and collagen in the homogeneous mixture. Nevertheless, thrombin stabilizers preferably selected from the group consisting of a polyol, a polysaccharide, a polyalkylene glycol, amino acids or mixtures thereof might be used according to the invention. The exemplary use of sorbitol, glycerol, polyethylene glycol, polypropylene glycol, mono- or disaccharides such as glucose or saccharose or any sugar or sulfonated amino acid capable of stabilizing thrombin activity is preferred.

Other examples of additives which can be used according to the present invention include substances such as vasoconstrictors, antibiotics or fucoidans.

A sponge of the present invention may further contains a dye, e.g. riboflavin, or other dye known from the prior art to be biocompatible. The dye may be included e.g. as a further layer (coating) and may especially help the surgeon to identify which one of the surfaces of a coated sponge of the present invention is the active or inactive surface, respectively.

The sponge of the present invention preferably has an overall thickness of less than 3 cm, preferably about 1 mm to about 3 cm, more preferably about 1 mm to about 2 cm, most preferred about 1 mm to about 2 mm.

In a sponge of the present invention the thickness of the coating is preferably from about 0.01 mm to about 1 mm.

The sponge of the present invention is preferably used in minimal invasive surgery, e.g. for laparoscopic application.

The sponge may be dried and after drying, the sponge may have a water content of at least 0.5 (percentages given in w/w here). In certain embodiments the sponge can be freeze-dried or air-dried.

The present invention also provides a wound coverage comprising a sponge according to the invention. The sponge and all additional layers can be provided in a ready to use wound coverage in suitable dimensions. The sponge and/or the coverage can be a pad or a sheet, preferably having a thickness of at least 1 mm or at least 2 mm a or at least 5 mm and/or up to 20 mm, depending on the indication. When the relatively thick flexible sponge is applied to a wound it is important that blood and fibrinogen can be absorbed throughout the sponge before fibrin is formed that might act as a barrier for the absorption of further wound secret.

Another aspect of the invention relates to a method of manufacturing a hemostatic sponge (=process I) comprising
a) providing a sponge comprising a matrix of a biomaterial in dried form,
b) providing one reactive polymeric material in the form of dry powder,
c) contacting a) and b) so that the material of b) is present on at least one surface of said sponge, and
d) fixing the material of b) on the sponge of a).

Fixing may be achieved by melting the polymeric component onto the sponge in a pre-heated oven, e.g. at temperatures between 30° C. to 80° C., preferably between 60° C. to 65° C. for a time period sufficient for fixing, e.g. between 1 minute to 10 minutes, preferably about 4 minutes. Alternatively fixing can be achieved by an infrared heater or any other heat source. The distance between the pad and the heater, the intensity of the heater and the time of exposure to infrared irradiation are adjusted to achieve melting of the coating at a minimum of heat exposure.

Another aspect of the invention relates to a method of manufacturing a hemostatic sponge (=process II) comprising
a) providing a sponge comprising a matrix of a biomaterial in dried form,
b) providing one reactive polymeric material in the form of a solution, e.g. an aqueous solution with a pH of lower than 5, preferably about 3 or a water free organic solvent based solution, e.g. based on ethanol, acetone, methylenechloride and the like,
c) contacting a) and b) so that the material of a) is impregnated with b), and
d) drying the material obtained in step c).

Contacting for achieving impregnation may be done by placing the polymeric solution on top of the sponge and let the solution be soaked into said sponge for a time period sufficient for said absorption, e.g. from about 2 minutes to about 2 hours, preferably 30 minutes.

Drying may include freeze drying or air drying and comprises removing volatile components of the fluid.

In another aspect the present invention provides a hemostatic sponge obtainable by a method of manufacturing according to process (I) or (II).

Another aspect of the invention relates to the use of a sponge of the present invention for the treatment of an injury selected from the group consisting of a wound, a hemorrhage, damaged tissue and/or bleeding tissue. Preferably a sponge of the present invention is used for the sealing of tissues, e.g. lung, spleen, liver; and for hemostasis.

The composite of the present invention can also be used as a ready to use tissue sealant, wherever the concentration of body fluids in proteins is high enough to allow the formation of a sealing gel as described above.

The sponge of the present invention is especially indicated in open and endoscopic/laparoscopic/thoracoscopic/MIS (minimal invasive surgery) surgical procedures as an adjunct to hemostatsis, to address surgical bleeding, from oozing to active, when control of bleeding by ligature or conventional procedures is ineffective or impractical.

In a preferred embodiment the sponge of the present invention is applied together with a buffer solution, e.g. an alkaline buffer solution, such as a bicarbonate solution, such as 8.4% $NaHCO_3$, pH 8.3, e.g. on a gauze.

It has been found that the speed of reaction is increased after application with 8.4% $NaHCO_3$-solution soaked gauze compared to saline soaked gauze. This was observed by an higher adherence of the sponge to the tissue after 2 minutes in the case of the $NaHCO_3$-application.

The present invention further provides a kit comprising a sponge of anyone claims 1 to 5 and a buffer solution, e.g. an alkaline buffer solution, such as a bicarbonate or carbonate, together with instructions for its use. The alkaline buffer solution preferably has a pH about 8, such as 8.3.

Another aspect of the present invention relates to a hemostatic composite comprising a water insoluble haemostatic material (matrix) and a hydrophilic polymeric cross-linker with reactive groups, said composite comprising pores which allow external fluids, especially human blood, to access into said composite. The haemostatic material may be any material mentioned above as "matrix of a biomaterial" which by itself already has a certain haemostatic property. Such materials are known in principle in the art as well as their haemostatic property. The composite material according to the present invention has pores which allow external fluids to access the inner part of the composite so that e.g. if applied to a wound, blood of this wound can enter the composite. The composite can get soaked by these pores. Practically important examples include non-woven or woven fabric of a haemostatic fiber or a porous haemostatic sponge. Preferably, this haemostatic material is a collagen sponge, a fabric of oxidized regenerated cellulose, a fibrin sponge or a gelatin sponge. It is specifically preferred, that the collagen sponge is essential native collagen (i.e. native collagen fiber structure is to a large extend preserved or regenerated by fibrillogenesis during processing).

The reactivity of the hydrophilic polymeric crosslinker in the composite according to the present invention is retained.

This means that the reactive groups of the crosslinker have not yet reacted with the (surface of the) haemostatic material and are not hydrolyzed by water. This can be achieved by combining the hemostatic material with the crosslinker in a way which does not lead to reaction of the reactive groups of the crosslinker with the hemostaic material or with water, e.g. as disclosed herein by melting, spraying, soaking under inert conditions, etc. Usually, this includes the omitting of aqueous conditions (or wetting), especially wetting without the presence of acidic conditions (if crosslinkers are not reactive under acidic conditions). This allows the provision of reactive haemostatic materials. Preferably, the haemostatic composite according to the present invention contains a polyethylene glycol (PEG) as hydrophilic polymeric crosslinker with reactive groups, especially a PEG comprising two or more, preferably 4, reactive groups selected from succinimidylesters ($-CON(COCH_2)_2$), aldehydes ($-CHO$) and isocyanates ($-N=C=O$), especially preferred succinimidylesters, such as component $COH10_2$ as defined below of Coseal.

In a preferred embodiment the matrix material which forms the porous network of the sponge constitutes of between 1-50%, 1-10%, or about 3% of the dried porous sponge (w/w-%).

The matrix of a biomaterial, especially the collagen, according to the present invention in general is not soluble, in particular not water-soluble. However, since the sponge is be porous and/or hygroscopic, it is allowed to swell when it is brought together with aqueous fluids, especially blood, serum, plasma, etc. or other fluids present in wounds and takes up these fluids.

The hemostatic sponge according to the present invention is fluid absorbing. "Fluid absorbing" shall be considered as the physical process to hold fluids upon contacting which may or may not provoke swelling of the sponge. Preferably the sponge can hold an amount of fluid, in particular blood, of at least 1 time, at least 2 times, at least 4 times or at least 10 times and/or up to 100 times, up to 20 times or up to 10 of the dry weight of the sponge. The sponge material according to the present invention can take up fluids even under pressure.

The porous sponge material according to the present invention preferably has a pore size of 5 to 500 µm, preferably of 10 to 200 µm. This pore size can properly be adjusted in the course of production of the sponge biomaterial, especially by way of directing a drying process in the course of such production.

The sponge according to the present invention is preferably provided in a "ready-to-use" form so that it is directly applicable to a patient in need thereof, e.g. to a wound of this patient (whereafter crosslinking starts). The sponge according to the present invention is therefore packed into a sterile package which protects the sponge from contamination (e.g. by moisture or microorganisms) during storage. Before use, the package can be opened (preferably also under sterile conditions) and the sponge can directly be applied to the patient ("ready-to use").

As already mentioned, the hydrophilic polymeric component is a hydrophilic crosslinker. According to a preferred embodiment, this crosslinker has more than two reactive groups for crosslinking ("arms"), for example three, four, five, six, seven, eight, or more arms with reactive groups for crosslinking. For example, NHS-PEG-NHS is an effective hydrophilic crosslinker according to the present invention. However, for some embodiments, a 4-arm polymer (e.g. 4-arms-p-NP-PEG) may be more preferred; based on the same rationale, an 8-arm polymer (e.g. 8-arms-NHS-PEG) may even be more preferred for those embodiments where multi-reactive crosslinking is beneficial. Moreover, the hydrophilic crosslinker according to the present invention is a polymer, i.e. a large molecule (macromolecule) composed of repeating structural units which are typically connected by covalent chemical bonds. Polymers according to the present invention should have a molecular weight of at least 1000 Da (to properly serve as crosslinkers for the sponge according to the present invention); preferably the crosslinking polymers according to the present invention has a molecular weight of at least 5000 Da, especially of at least 8000 Da.

For some hydrophilic crosslinkers, the presence of basic reaction conditions (e.g. at the administration site) is preferred or necessary for functional performance (e.g. for a faster crosslinking reaction at the administration site). For example, carbonate or bicarbonate ions (e.g. as a buffer with a pH of 7.6 or above, preferably of 8.0 or above, especially of 8.3 and above) may be additionally provided at the site of administration (e.g. as a buffer solution or as a fabric or pad soaked with such a buffer), so as to allow an improved performance of the sponge according to the present invention or to allow efficient use as a hemostatic and/or wound adherent material.

Figure 1:
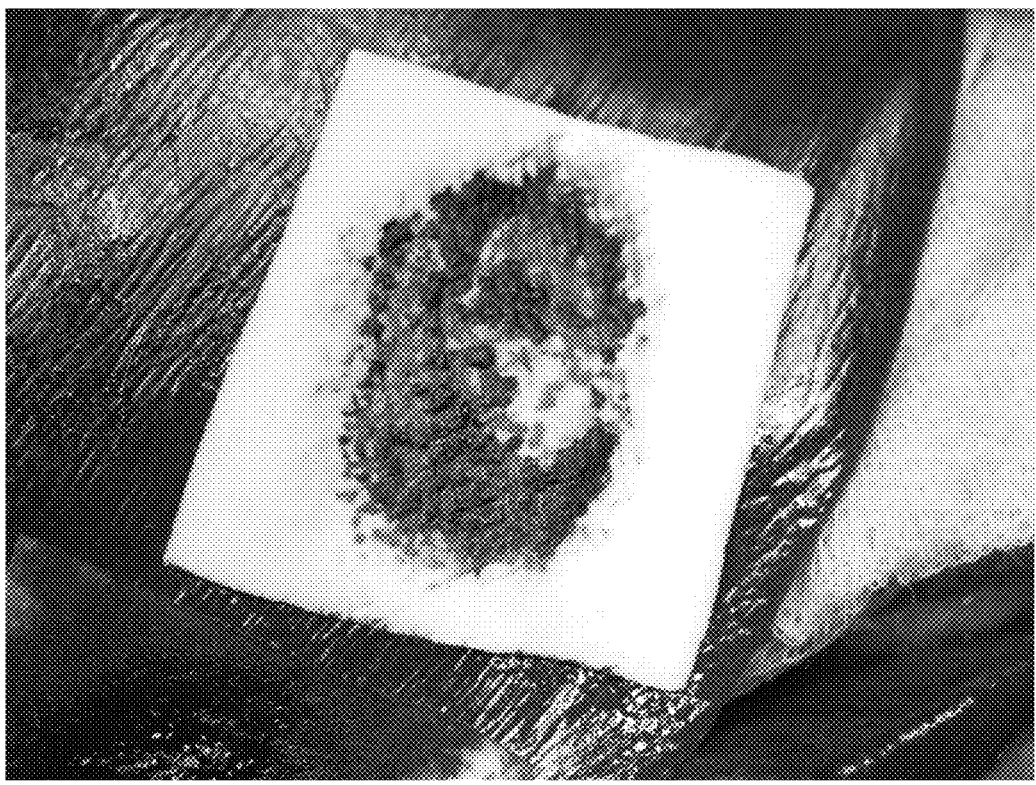
FIG. 1: Hemostatic efficacy of a collagen pad coated with NHS-PEG A hemostatic pad is produced according to example 2 and coated with 14 mg/cm$^2$ COH102 (as defined below). The hemostatic efficacy is evaluated according to the animal as described below. The bleeding is stopped 2 min after the pad application. No rebleeding is observed.
Figure 2:
FIG. 2: Hemostatic efficacy of a collagen pad impregnated with NHS-PEG A hemostatic pad is produced according to example 3 and impregnated with 8 mg/cm$^2$ COH 102. The hemostatic efficacy is evaluated according to the animal as described below. The bleeding is stopped 2 min after the pad application. No rebleeding is observed.
Figure 3:
FIG. 3: Hemostatic efficacy of a collagen pad containing oxidized cellulose fabric coated with NHS-PEG
A hemostatic pad is produced according to example 5 and coated with 14 mg/cm$^2$ COH102. The hemostatic efficacy is evaluated according to the animal as described below. The bleeding is stopped 2 min after the pad application. No rebleeding is observed.
Figure 4:
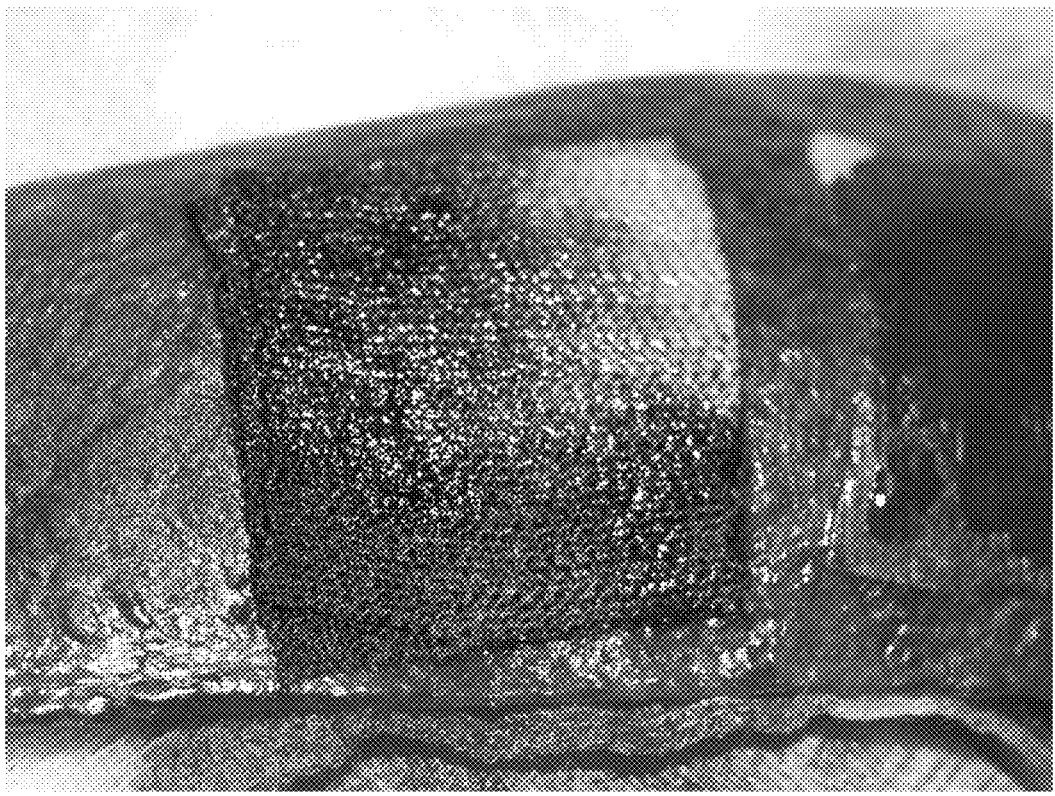
FIG. 4: Hemostatic efficacy of an oxidized cellulose fabric coated with NHS-PEG A hemostatic pad is produced according to example 6 and coated with 14 mg/cm$^2$ COH102. The hemostatic efficacy is evaluated according to the animal as described below. The bleeding is stopped 2 min after the pad application. No rebleeding is observed.
Figure 5:
FIG. 5: Hemostatic efficacy of a collagen pad containing fucoidan as hemostasis enhancing substance coated with NHS-PEG
A hemostatic pad is produced according to example 7 and coated with 14 mg/cm$^2$ COH102. The hemostatic efficacy is evaluated according to the animal as described below. The bleeding is stopped 2 min after the pad application. No rebleeding is observed.

In the subsequent sections the following abbreviations are used:
ACT activated coagulation time
AcOH acetic acid
NaOAc sodium acetate
aq. aqueous
COH102 Pentaerythritolpoly(ethyleneglycol)ether tetrasuccinimidyl glutarate=Pentaerythritol tetrakis[1-1'-oxo-5'-succinimidylpentanoate-2-poly oxoethyleneglycolejether (=an NHS-PEG with MW 10,000)
EtOH ethanol
PEG polyethylene glycol
PET polyethylene terephthalate
min minutes
NHS-PEG-NHS A-[6-[(2,5-dioxo-1-pyrrolidinyl)oxy]-6-oxohexyl]-ω-[6-[(2,5-dioxo-1-pyrrolidinyl)oxy]-6-oxo-hexyloxy]-polyoxyethylene
8-arms-NHS-PEG Hexaglycerol octa(succinimidyloxyglutaryl)polyoxyethylene
4-arms-p-NP-PEG Pentaerythrioltetra(4-nitrophenoxycarbonyl) polyoxyethylene
CHO-PEG-CHO homobifunctional aldehyd-polyethylenglycole
Epoxy-PEG-Epoxy homobifunctional epoxy-polyethylenglycole
4-arm-Epoxy-PEG homomultifunctional epoxy polyethylenglycole
ISC-PEG-ISC homobifunctional isocyanate-polyethylenglycole
AA-dextran aldehyde-activate dextran
DSS Disuccinimidyl suberate
EGS Ethylene glycol-bis(succinic acid N-hydroxysuccinimide ester)

EXAMPLES

Animal Hemostasis Model for Testing the Efficacy of Hemostatic Pads of the Present Invention (Liver Surface Abrasion Model)

The efficacy of the hemostatic pads of the present invention is tested in a liver surface abrasion model on heparinized (2×ACT) pigs. With a flat, round, rotating abrasion tool a circular bleeding wound (1.8 cm diameter) is created on the liver surface. A pad of the present invention (size=3×3 cm) is applied in its dry state onto the bleeding wound and hold in place by exerting slight pressure with a saline wetted gauze for 2 min. The efficacy in stopping the bleeding is evaluated.

Example 1

Preparation of Bovine Collagen Suspension 50 g of sliced bovine corium are dispersed in 500 ml of a 2M NaOH-solution and stirred approx. 90 min at 25° C. The corium is sieved out and rinsed with distilled $H_2O$ until effluent $H_2O$ reaches a pH of about 8.0. The washed corium slices are re-suspended in $H_2O$ and the pH is adjusted with HCl to approx. 2.0. The suspension obtained is stirred overnight at approx. 25° C. and a collagen solution is obtained. The solution obtained is cooled to 5° C. and the pH is adjusted with NaOH to neutral. Collagen precipitation is carried out overnight by keeping the solution at 18° C. without stirring. Precipitated collagen obtained is separated by filtration. The collagen concentration of the material obtained is determined by gravimetry. Optionally a chemical crosslinking with glutaraldehyde may be carried out in that a 1% aq. collagen suspension is prepared and 5000 ppm of glutaraldehyde are added at 12° C. The suspension obtained is stirred overnight. Crosslinked collagen obtained is filtered and washed with $H_2O$. The collagen concentration of the material obtained is determined as described above.

Example 2

Collagen Pad Coated with NHS-PEG

COH102 powder is homogeneously distributed onto one surface of a commercially available collagen sponge (Matristypt®, Dr. Suwelack Skin- and Healthcare, Germany, thickness 1 mm or 2 mm). COH102 amounts of 2 mg/cm², 7 mg/cm², 10 mg/cm², 14 mg/cm², mg/cm² are used for the coating. The COH102 powder is fixed on the surface of the sponge by melting. This is performed at 60° C. to 65° C. for 4 min by placing the sponge with the PEG powder mixture into a preheated oven.

A dried sponge obtained is sealed together with a sachet of desiccant in a gas-impermeable pouch and γ-sterilized at 25 kGray.

Example 3

Collagen Pad Impregnated with NHS-PEG

Aq, acidic solutions (pH 3.0, AcOH) of COH102 with concentrations of 10 mg/cm³, 20 mg/cm³, 30 mg/cm³ and 40 mg/cm³ are prepared and filled into 9×7 cm PET-trays. Commercial available bovine collagen sponges (Matristypt®), 9×7×0.1 or 0.2 cm, with the same volume as the previously filled COH102 solution are placed on the top of the solutions for impregnation for 20 min. COH102 solution is absorbed and the collagen material obtained is lyophilized. Sponges obtained can be additionally coated with COH102 as described in example 2.

After lyophilization and/or coating each dried sponge obtained is sealed together with a sachet containing desiccant in a gas impermeable pouch and sterilized by γ-irradiation at 25 kGray.

Example 4

Collagen Pad Containing Oxidized Cellulose Powder Coated with NHS-PEG 0.5 g or 19 Traumastem® P powder (Bioster, Czech Republic) is homogenously distributed into 22 ml of neutral aqueous collagen suspension (2.15 mg/ml; 4.3 mg/ml and 10 mg/ml) produced according to example 1. The mixture obtained is filled into flat 9×7 cm PET trays and lyophilized. A fleece obtained has a thickness of about 3-4 mm and is coated with COH102 as described in example 2.

After coating, each sponge obtained is sealed together with a sachet containing desiccant in a gas impermeable pouch and sterilized by γ-irradiation at 25 kGray.

Example 5

Collagen Pad Containing Oxidized Cellulose Fabric Coated with NHS-PEG

A 6×5 cm Traumastem® TAF light-fabric (Bioster. Czech Republic) is immersed into a 1% bovine collagen suspension as described in example 1. The 6×5 cm oxidized cellulose fabric retains approximately 6 g of the collagen suspension. A fabric soaked with the collagen suspension is obtained and laid in a tray and lyophilized. A fleece obtained has a thickness of about 3-4 mm and is coated with COH102 as described in example 2.

After coating, each sponge obtained is sealed together with a sachet containing desiccant in a gas impermeable pouch and sterilized by γ-irradiation at 25 kGray.

Example 6

Oxidized Cellulose Fabric Coated with NHS-PEG

A double layer Traumastem® P fleece (Bioster, Czech Republic) is coated with 14 mg/cm$^2$ COH102 as described in example 2. The thickness of the pad obtained is about 1-2 mm.

Example 7

Collagen Pad Containing Fucoidan as Hemostasis Enhancing Substance Coated with NHS-PEG A bovine collagen sponge Matristypt® (9×7×0.2 cm) is impregnated with the same volume of a Fucoidan solution of A. nodosum (10 μM and 200 μM in 40 mM Ca$^{2+}$-solution) and lyophilized. A sponge obtained is coated with COH102 as described in example 2.

Example 8

Collagen Pad Containing Thrombin as Hemostasis Enhancing Substance Coated with NHS-PEG A bovine collagen sponge Matristypt® (9×7×-0.2 cm) is impregnated with the same volume of a thrombin solution (500 IU/ml) and lyophilized. A sponge obtained is coated with COH102 as described in example 2.

Example 9

Sealing Efficacy of a Collagen Pad Coated with NHS-PEG

Figure 6:
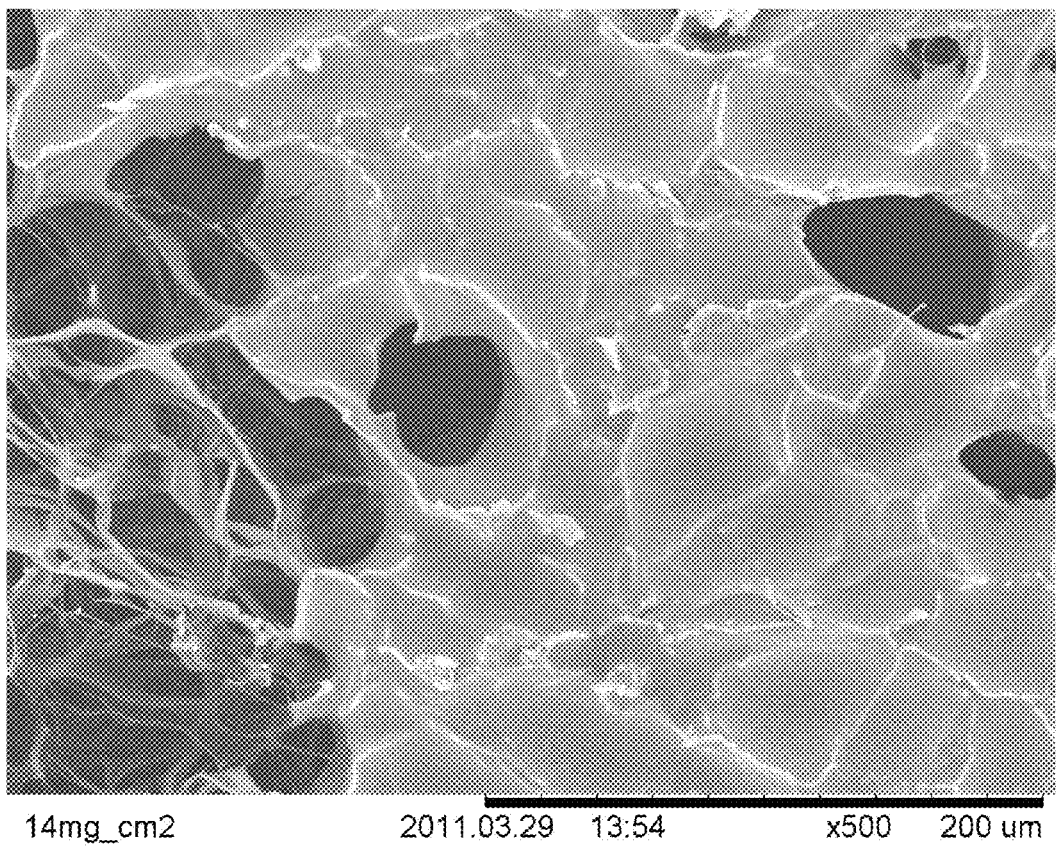
FIG. 6: Scanning electron microscopy image (magnification: ×500) of the surface of a discontinuously coated collagen sponge
Figure 7:
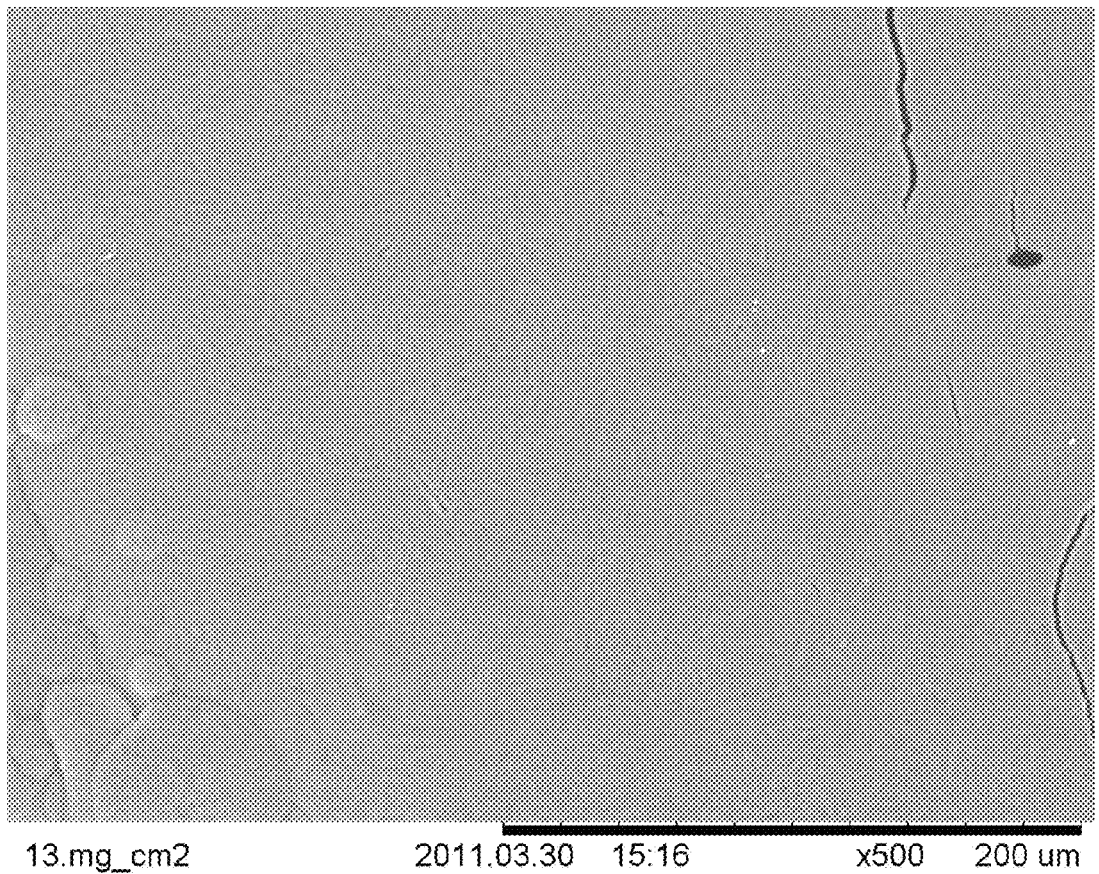
FIG. 7: Scanning electron microscopy image (magnification: ×500) of the surface of a continuously coated collagen sponge
Figure 8:
FIG. 8: Gelfoam coated with 14 mg/cm$^2$ COH102 in the liver lobe abrasion model

A hemostatic pad coated with 14 mg/cm$^2$ COH102 is produced according to example 2. A lesion of around 1.5 to 2 cm in diameter is set by a scalpel on the lung of a pig. A sample of 3×3 cm of the said pad is applied onto the wound and hold in place by exerting slight pressure with the aid of gauze for 2 min. The gauze is pre-wetted either with saline or basic bicarbonate solution (pH 8.3). After application, the pad is adhering firmly to the lung surface (see FIG. 6). The speed of obtaining adherence is increased using gauze wetted with bicarbonate. In order to control the air tightness and the pad-adherence to the tissue the chest is filled with Ringer's solution after 10 min. No gas leakage or detachment of the pad is observed.

Example 10

Sealing Efficacy of a Collagen Pad Impregnated with NHS-PEG

A hemostatic pad impregnated with 40 mg/cm$^3$ COH102 is produced according to example 3.

A lesion of around 1.5 to 2 cm in diameter is set by a scalpel on the lung of a pig. A sample of 3×3 cm of the said pad is applied onto the wound and hold in place by exerting slight pressure with the aid of gauze for 2 min. The gauze is pre-wetted with basic bicarbonate solution (pH 8.3). After application the pad is adhering firmly to the lung surface. Air tightness and pad-adherence to the tissue are determined as described in Example 9.

Example 11

Color Marking of One Pad Surface

A mask made of a stainless steel plate (1 mm thickness) with a pattern of holes is placed on one side of a 1 or 2 mm thick collagen sponge (Matristypt®,), Dr. Suwelack Skin- and Healthcare, Germany). The holes of the mask have a diameter of 2 mm and are placed at a distance of 1 cm from each other in the nodes of an upright square lattice. A 0.5% aqueous Erioglaucine (Fluka, Switzerland) solution is sprayed with a standard airbrush device over the holes of the mask. The mask is removed and a collagen sheet with the blue dot pattern obtained is dried at ambient atmosphere, in a vacuum oven or in a desiccator. The dot pattern on one side has the role to distinguish the active and inactive surface of a coated pad. It is possible to apply the coating either on the dotted side or the non-dotted side.

Example 12

Preparation of a Fibrin Fleece

A solution of 2.5 mg/ml of fibrinogen, 10 mM Tris/HCl, 150 mM NaCl, pH 7.4 and an equal volume of 55 IU thrombin/ml, 10 mM CaCl$_2$ are mixed using a static mixer and immediately filled into a tray at a height of 0.7 cm. A fibrin clot is obtained in the tray. By freeze-drying of the clot a fibrin fleece is obtained.

Example 13

Preparation of Collagen Pad Coated with NHS-PEG-NHS and its Testing in Animal Model On the non-colored side of a 6×6 cm collagen pad (made as described in example 11) 14 mg/cm$^2$ and 28 mg/cm$^2$ of bifunctional NHS-PEG-NHS (MW 10000, NOF Corporation, Japan) are homogeneously distributed and fixed by melting. This is performed at approx. 70° C. for 4 min by placing the sponge coated with the PEG powder into a preheated oven. Sponges obtained are sealed together with a sachet containing desiccant in a gas-impermeable pouch.

The hemostatic performance of said pads are tested in pig in the liver abrasion model as described above. After 2 minutes hemostasis is achieved. No rebleeding after 10 minutes is observed. The adherence of the pad on the tissue is sufficient.

Example 14

Preparation of Collagen Pad Coated with 8-Arm-NHS-PEG and its Testing in Animal Model On the non-colored side of a 6×6 cm collagen pad, made as described in example 11, 14 mg/cm$^2$ 8-arm-NHS-PEG (MW 15000, NOF Corporation, Japan) are homogeneously distributed and fixed by melting. This is performed at 65° C. for 4 min by placing the sponge with the PEG powder into a preheated oven.

A sponge obtained is sealed together with a sachet containing desiccant in a gas-impermeable pouch.

The hemostatic performance of said pad is tested in pig in the liver abrasion model as described above. After 2 minutes hemostasis is achieved. No rebleeding after 10 minutes is observed. The adherence of the pad on the tissue is sufficient.

Example 15a

Preparation of Collagen Pad Coated with 4-Arm-p-NP-PEG and its Testing in Animal Model On the non-colored side of a 6×6 cm collagen pad, made as described in example 11, 14 mg/cm$^2$ 4-arm-p-NP-PEG (MW 10000, NOF Corporation, Japan) are homogeneously distributed and fixed by melting. This is performed at 65° C. for 4 min by placing the sponge with the PEG powder into a preheated oven.

A sponge obtained is sealed together with a sachet containing desiccant in a gas-impermeable pouch.

The hemostatic performance of the said pad is tested in pig in the liver abrasion model as described above. After 2 minutes hemostasis is achieved. No rebleeding after 10 minutes is observed. The adherence of the pad on the tissue is not sufficient.

Example 15b

Preparation of Collagen Pad Coated with 4-Arm-p-NP-PEG and its Testing in Animal Model The hemostatic performance of the pad as prepared in Ex. 15a is tested in pig in the liver abrasion model as described above but with the modification, that the pad is applied with gauze pre-wetted with basic 8% Na-bicarbonate solution. After 2 minutes hemostasis is achieved. No rebleeding after 10 minutes is observed. The adherence of the pad on the tissue is sufficient.

Example 16a

Preparation of Collagen Pad Coated with CHO-PEG-CHO and its Testing in Animal Model On the non-colored side of a 6×6 cm collagen pad, made as described in example 11, 9.5 mg/cm$^2$ CHO-PEG-CHO (MW 3400, Interchim, France) are homogeneously distributed and fixed by melting. This is performed at 70° C. for 4 min by placing the sponge with the PEG powder into a preheated oven.

A sponge obtained is sealed together with a sachet containing desiccant in a gas-impermeable pouch.

The hemostatic performance of said pad is tested in pig in the liver abrasion model as described above. After 2 minutes hemostasis is achieved. No rebleeding after 10 minutes is observed. The adherence of the pad on the tissue is sufficient.

Example 16b

Preparation of Collagen Pad Coated with CHO-PEG-CHO and its Testing in Animal Model The hemostatic performance of the pad as prepared in EX. 16a is tested in pig in the liver abrasion model as described above but with the modification, that the pad is applied with gauze pre-wetted with basic Na-bicarbonate solution. After 2 min hemostasis is achieved. No rebleeding after 10 min is observed. The adherence of the pad on the tissue is sufficient.

Example 17a

Preparation of Collagen Pad Coated with Epoxy-PEG-Epoxy and its Testing in Animal Model On the non-colored side of a 6×6 cm collagen pad made, as described in example 11. 9.5 mg/cm$^2$ Epoxy-PEG-Epoxy (MW 3400, Interchim, France) are homogeneously distributed and fixed by melting. This is performed at 70° C. for 4 min by placing the sponge with the PEG powder into a preheated oven.

A sponge obtained is sealed together with a sachet containing desiccant in a gas-impermeable pouch.

The hemostatic performance of said pad is tested in pig in the liver abrasion model as described above. After 2 min no hemostasis is achieved. The adherence of the pad on the tissue is not sufficient.

Example 17b

Preparation of Collagen Pad Coated with Epoxy-PEG-Epoxy and its Testing in Animal Model The hemostatic performance of the pad as prepared in Ex. 17a is tested in pig in the liver abrasion model as described above but with the modification, that the pad is applied with gauze pre-wetted with basic Na-bicarbonate solution. After 2 min hemostasis is achieved. No rebleeding after 5 min is observed. The adherence of the pad on the tissue is sufficient.

Example 18

Preparation of Collagen Pad Coated with 4-Arm-Epoxy-PEG and its Testing in Animal Model On the non-colored side of a 6×6 cm collagen pad, made as described in example 11, 14 mg/cm$^2$ 4-arm-epoxy-PEG (MW 10000, Interchim. France) are homogeneously distributed and fixed by melting. This is performed at 70° C. for 4 min by placing the sponge with the PEG powder into a preheated oven.

A sponge obtained is sealed together with a sachet containing desiccant in a gas-impermeable pouch.

The hemostatic performance of said pad is tested in pig in the liver abrasion model as described above, but with the modification, that the pad is applied with gauze pre-wetted with basic Na-bicarbonate solution. After 2 min hemostasis is achieved. No rebleeding after 5 min is observed.

The adherence of the pad on the tissue is sufficient.

Example 19

Preparation of Collagen Pad Coated with ISC-PEG-ISC and its Testing in Animal Model On the non-colored side of a 6×6 cm collagen pad, made as described in example 11. 9.5 mg/cm$^2$ ISC-PEG-ISC (MW 3400, Interchim. France) are homogeneously distributed and fixed by melting. This is performed at 70° C. for 4 min by placing the sponge with the PEG powder into a preheated oven.

A sponge obtained is sealed together with a sachet containing desiccant in a gas-impermeable pouch.

The hemostatic performance of said pad is tested in pig in the liver abrasion model as described above. After 2 min hemostasis is achieved. No rebleeding after 10 min is observed.

The adherence of the pad on the tissue is sufficient.

Example 20

Preparation of Collagen Pad Coated with AA-Dextran and its Testing in Animal Model On the non-colored side of a 6×6 cm collagen pad made as described in example 11 14 mg/cm$^2$ of a mixture of 0.1 mg/cm$^2$ AA-dextran (MW 40000, Pierce. USA) and 13.9 mg/cm$^2$ unsubstituted PEG (MW 10000, Sigma Aldrich, Germany) are homogeneously distributed and fixed by melting. This is performed at 80° C. for 4 min by placing the sponge with the powder mixture into a preheated oven.

A sponge obtained is sealed together with a sachet containing desiccant in a gas-impermeable pouch.

The hemostatic performance of said pad is tested in pig in the abrasive liver lobe model as described above but with the modification, that the pad is applied with gauze pre-wetted with basic Na-bicarbonate solution. After 2 min hemostasis is achieved. No rebleeding after 10 min is observed. The adherence of the pad on the tissue is sufficient.

Example 21a

Preparation of Collagen Pad Coated with DSS and its Testing in Animal Model

On the non-colored side of a 6×6 cm collagen pad made as described in example 11 20 mg/cm$^2$ of a 1:1 mixture of DSS (MW 368.35, Sigma Aldrich, Germany) and unsubstituted PEG (MW 10000, Sigma Aldrich, Germany) are homogeneously distributed and fixed by melting. This is performed at 80° C. for 4 min by placing the sponge with the powder mixture into a preheated oven.

A sponge obtained is sealed together with a sachet containing desiccant in a gas-impermeable pouch.

The hemostatic performance of said pad is tested in pig in the abrasive liver lobe model as described above. After 2 min hemostasis is not achieved. The adherence of the pad on the tissue is not sufficient.

Example 21b

Preparation of Collagen Pad Coated with DSS and its Testing in Animal Model

The hemostatic performance of the pad as prepared in Ex. 21a is tested in pig in the abrasive liver lobe model as described above but with the modification, that the pad is applied with gauze pre-wetted with basic bicarbonate solution. After 2 min hemostasis is achieved. No rebleeding after 10 min is observed. The adherence of the pad on the tissue is sufficient.

Example 22a

Preparation of Collagen Pad Coated with EGS and its Testing in Animal Model

On the non-colored side of a 6×6 cm collagen pad made as described in example 11 26 mg/cm$^2$ of a 1:1 mixture of EGS (MW 456.36, Sigma Aldrich, Germany) and unsubstituted PEG (MW 10000, Sigma Aldrich, Germany) are homogeneously distributed and fixed by melting. This is performed at 80° C. for 4 min by placing the sponge with the powder mixture into a preheated oven.

A sponge obtained is sealed together with a sachet containing desiccant in a gas-impermeable pouch.

The hemostatic performance of said pad is tested in pig in the liver abrasion model as described above. After 2 min hemostasis is not achieved. The adherence of the pad on the tissue is not sufficient.

Example 22b

Preparation of Collagen Pad Coated with EGS and its Testing in Animal Model

The hemostatic performance of the pad as prepared in Ex. 22a is tested in pig in the liver abrasion model as described above but with the modification, that the pad is applied with gauze pre-wetted with basic Na-bicarbonate solution. After 2 min hemostasis is achieved. No rebleeding after 10 min is observed. The adherence of the pad on the tissue is sufficient.

Example 23

Fibrin Fleece Coated with NHS-PEG

On one side of the fibrin fleece, made as described in example 12, 14 mg/cm$^2$ of COH102 are homogeneously distributed and fixed by melting. This is performed at 65° C. for 4 min by placing the sponge with the PEG powder into a preheated oven.

A sponge obtained is sealed together with a sachet containing desiccant in a gas-impermeable pouch.

The hemostatic performance of said pad is tested in pig in the liver abrasion model as described above. After 2 min hemostasis is achieved. No rebleeding after 10 min is observed. The adherence of the pad on the tissue is sufficient.

Example 24

Correlation Between the Adherence Force to the Tissue and the Cross-Linker Used for Collagen Pad Coating After application of the pads to the bleeding tissue in the liver abrasion model the adherence of the pad to the liver tissue is evaluated. Slight tangential force is applied with the lateral part of a forceps. Presence of adherence (bonding to the tissue) is considered if it is not possible to displace the pad from the site of application. Adherence score: 1=no displacement at 5 min after application; 2=no displacement 10 min after application; 3=displacement (no adherence) 10 min after application.

| Example No. | Cross-linker | Adherence score |
| --- | --- | --- |
| 13 | NHS-PEG-NHS | 1 |
| 14 | 8-arms-NHS-PEG | 1 |
| 15a | 4-arms-p-NP-PEG | 3 |
| 15b | 4-arms-p-NP-PEG - basic application | 2 |
| 16a | CHO-PEG-CHO | 1 |
| 16b | CHO-PEG-CHO - basic application | 2 |
| 17a | Epoxy-PEG-Epoxy | 3 |
| 17b | Epoxy-PEG-Epoxy - basic application | 2 |

-continued

| Example No. | Cross-linker | Adherence score |
|---|---|---|
| 18 | 4-arm-Epoxy-PEG - basic application | 2 |
| 19 | ISC-PEG-ISC | 1 |
| 20 | AA-dextran - basic application | 1 |
| 21a | DSS | 3 |
| 21b | DSS - basic application | 2 |
| 22a | EGS | 3 |
| 22b | EGS - basic application | 2 |

Example 25

Chitosan/Gelatine Sponge Coated with NHS-PEG and its Testing in Animal Model

On a commercially available chitosan/gelatin sponge (Chitoskin®, Beese Medical, Germany) 14 mg/cm² of COH102 are homogeneously distributed and fixed by melting. This is performed at 65° C. for 4 min by placing the sponge with the PEG powder into a preheated oven.

A sponge obtained is sealed together with a sachet containing desiccant in a gas-impermeable pouch.

Figure 9:
FIG. 9: Chitoskin coated with 14 mg/cm² COH102 in the liver lobe abrasion model The present invention is further exemplified by the following examples without being limited thereto.

The hemostatic performance of said pad is tested in pig in the liver abrasion model as described above. After 2 min hemostasis is achieved. No rebleeding after 10 min is observed (FIG. 9).

The adherence of the pad on the tissue is sufficient.

Example 26

Preparation of a Gelatin Pad Coated with NHS-PEG and its Testing in Animal Model On a commercially available gelatin sponge (Gelfoam®, Pfizer, USA) 14 mg/cm² COH102 are homogeneously distributed and fixed by melting. This is performed at approx. 70° C. for 4 min by placing the sponges coated with the PEG powder into a preheated oven.

The sponge obtained is sealed together with a sachet containing desiccant in a gas-impermeable pouch.

The hemostatic performance of said pads are tested in pig in the liver surface abrasion model as described above. After 10 minutes hemostasis is not achieved due to a lack of adherence on the tissue and slow liquid uptake of the sponge.

Example 27

Water Uptake Velocities

A 2×2 cm piece of a dry collagen sponge (Matristypt®, Dr. Suwelack, Germany) or of a dry cross-linked gelatin sponge (Gelfoam®, Pfizer) are placed onto the surface of distilled $H_2O$ into a beaker. The dry sponges are floating on the water surface and take up water over the 2×2 cm contact surface. After 6 s Matristypt® is totally soaked by $H_2O$ and removed from the water surface. The thicker Gelfoam® sponge is not totally soaked by $H_2O$ after 13 s, but removed after 13s from the water surface. From the weights of the 2×2 cm sponges before and after the contact with the water surface, the time of contact with the water surface and the area of contact with the water surface the initial water uptake velocities of the sponges (in mg water/s) per surface of contact (in cm²) is calculated. The initial water uptake velocities are 35 $mg \times cm^{-1} s^{-1}$ for Matristypt® and 0.8 $mg \times cm^{-1} s^{-1}$ for Gelfoam®.

What is claimed is:

1. A hemostatic porous composite sponge, comprising:
 a matrix of a biomaterial; and
 a single hydrophilic polymeric component comprising one or more reactive groups,
 wherein the matrix and the single hydrophilic polymeric component are associated with each other so that:
 the reactivity of the single hydrophilic polymeric component is retained.

2. The hemostatic porous composite sponge claim 1, wherein the biomaterial is selected from the group consisting of collagen, gelatin, fibrin, a polysaccharide, a synthetic biodegradable biomaterial, and derivatives thereof.

3. The hemostatic porous composite sponge of claim 2, wherein the polysaccharide comprises chitosan.

4. The hemostatic porous composite sponge of claim 2, wherein the synthetic biodegradable biomaterial comprises polylactic acid or polyglycolic acid.

5. The hemostatic porous composite sponge of claim 1, wherein the single hydrophilic polymeric component comprises a polyalkylene oxide polymer.

6. The hemostatic porous composite sponge of claim 5, wherein the polyalkylene oxide polymer comprises polyethylene glycol (PEG).

7. The hemostatic porous composite sponge of claim 5, wherein the polyalkylene oxide polymer comprises a multi-electrophilic polyalkylene oxide polymer.

8. The hemostatic porous composite sponge of claim 5, wherein the polyalkylene oxide polymer comprises a multi-electrophilic polyethylene glycol (PEG).

9. The hemostatic porous composite sponge of claim 5, wherein the polyalkylene oxide polymer comprises pentaerythritolpoly(ethyleneglycol)ether tetrasuccinimidyl glutarate.

10. The hemostatic porous composite sponge of claim 1, wherein the biomaterial is collagen, wherein the polymeric component is pentaerythritolpoly(ethyleneglycol)ether tetrasuccinimidyl glutarate, and wherein the single hydrophilic polymeric component is coated onto the collagen.

11. The hemostatic porous composite sponge of claim 1, wherein the biomaterial is collagen, wherein the polymeric component is pentaerythritolpoly(ethyleneglycol)ether tetrasuccinimidyl glutarate, and wherein the single hydrophilic polymeric component is impregnated into the collagen.

12. The hemostatic porous composite sponge claim 1, wherein the single hydrophilic polymeric crosslinker is coated onto a surface of the matrix.

13. The hemostatic porous composite sponge of claim 1, wherein the matrix is impregnated with the single hydrophilic polymeric crosslinker.

14. The hemostatic porous composite sponge claim 1, wherein the matrix is impregnated with the single hydrophilic polymeric crosslinker, and wherein the single hydrophilic polymeric crosslinker is coated onto a surface of the matrix.

15. A method of treating an injury, comprising:
 administering a hemostatic porous composite sponge to the injury, the sponge comprising:
 a matrix of a biomaterial; and
 a single hydrophilic polymeric component comprising one or more reactive groups,
 wherein the matrix and the single hydrophilic polymeric component are associated with each other so that:
 the reactivity of the single hydrophilic polymeric component is retained and
 wherein the injury comprises a member selected from the group consisting of a wound, a hemorrhage, a damaged tissue, and a bleeding tissue.

16. The method of claim 15, wherein the sponge is applied to the injury together with a buffer solution.

17. The method of claim 16, wherein the buffer solution comprises a bicarbonate solution.

18. The method of claim 16, wherein the buffer solution is present on a gauze.

19. The method of treating an injury of claim 15, wherein the single hydrophilic polymeric crosslinker is coated onto a surface of the matrix.

20. The method of treating an injury of claim 15, wherein the matrix is impregnated with the single hydrophilic polymeric crosslinker.

21. The method of treating an injury of claim 15, wherein the matrix is impregnated with the single hydrophilic polymeric crosslinker, and wherein the single hydrophilic polymeric crosslinker is coated onto a surface of the matrix.

22. A kit, comprising:
    a hemostatic porous composite sponge, comprising:
        a matrix of a biomaterial; and
        a single hydrophilic polymeric component comprising one or more reactive groups,
    wherein the matrix and the single hydrophilic polymeric component are associated with each other so that:
        the reactivity of the single hydrophilic polymeric component is retained,
    a buffer solution; and
    instructions for using the hemostatic porous composite sponge and the buffer solution.

23. The kit of claim 22, wherein the buffer solution comprises an alkaline buffer solution.

24. The kit of claim 23, wherein the alkaline buffer solution comprises a bicarbonate.

25. The kit of claim 22, wherein the single hydrophilic polymeric crosslinker is coated onto a surface of the matrix.

26. The kit of claim 22, wherein the matrix is impregnated with the single hydrophilic polymeric crosslinker.

27. The kit of claim 22, wherein the matrix is impregnated with the single hydrophilic polymeric crosslinker, and wherein the single hydrophilic polymeric crosslinker is coated onto a surface of the matrix.

* * * * *